(12) United States Patent
DeBenedictis et al.

(10) Patent No.: US 7,282,060 B2
(45) Date of Patent: *Oct. 16, 2007

(54) METHOD AND APPARATUS FOR MONITORING AND CONTROLLING LASER-INDUCED TISSUE TREATMENT

(75) Inventors: Leonard C DeBenedictis, Palo Alto, CA (US); Thomas R Myers, Palo Alto, CA (US); Kin F Chan, San Jose, CA (US); George Frangineas, Jr., Fremont, CA (US)

(73) Assignee: Reliant Technologies, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/020,648

(22) Filed: Dec. 21, 2004

(65) Prior Publication Data
US 2005/0154380 A1 Jul. 14, 2005

Related U.S. Application Data

(63) Continuation-in-part of application No. 10/745,761, filed on Dec. 23, 2003, and a continuation-in-part of application No. 10/750,790, filed on Dec. 31, 2003, now Pat. No. 7,184,184.

(60) Provisional application No. 60/605,092, filed on Aug. 26, 2004.

(51) Int. Cl.
*A61N 5/06* (2006.01)
(52) U.S. Cl. ............................. 607/88; 128/898; 606/9
(58) Field of Classification Search ................ 128/898; 606/9; 607/88–94
See application file for complete search history.

(56) References Cited

U.S. PATENT DOCUMENTS

| | | | |
|---|---|---|---|
| 3,619,033 A | 11/1971 | McMahon |
| 3,622,743 A | 11/1971 | Muncheryan |
| 3,721,486 A | 3/1973 | Bramley |
| 4,129,355 A | 12/1978 | Noguchi |
| 4,289,371 A | 9/1981 | Kramer |
| 4,387,952 A | 6/1983 | Slusher |
| 4,428,643 A | 1/1984 | Kay |
| 4,653,495 A | 3/1987 | Nanaumi |

(Continued)

FOREIGN PATENT DOCUMENTS

EP  0880941 B1  12/2001

(Continued)

OTHER PUBLICATIONS

Notification Of Transmittal Of The International Search Report And The Written Opinion Of The International Searching Authority, Or The Declaration, PCT/US2004/043749, Jun. 1, 2005.

(Continued)

*Primary Examiner*—Henry M Johnson, III
(74) *Attorney, Agent, or Firm*—Fenwick & West LLP

(57) ABSTRACT

The present invention provides methods and apparatus for controlling light-induced tissue treatment. In accordance with various aspects of the present invention, the invention provides for improved, real-time control of the light beam operational parameters which enables greater safety, efficiency, uniformity and continuity of the treatment process.

25 Claims, 17 Drawing Sheets

U.S. PATENT DOCUMENTS

| | | | |
|---|---|---|---|
| 4,718,416 A | 1/1988 | Nanaumi | |
| 4,733,660 A | 3/1988 | Itzkan | |
| 4,976,709 A | 12/1990 | Sand | |
| 5,000,752 A | 3/1991 | Hoskin et al. | |
| 5,018,803 A | 5/1991 | Hecker et al. | |
| 5,192,278 A | 3/1993 | Hayes et al. | |
| 5,282,797 A | 2/1994 | Chess | |
| 5,312,396 A | 5/1994 | Feld et al. | |
| 5,336,217 A | 8/1994 | Buys et al. | |
| 5,349,371 A | 9/1994 | Fong | |
| 5,423,803 A | 6/1995 | Tankovich et al. | |
| 5,474,549 A | 12/1995 | Ortiz et al. | |
| 5,501,680 A | 3/1996 | Kurtz et al. | |
| 5,555,130 A | 9/1996 | Marom et al. | |
| 5,558,666 A | 9/1996 | Dewey et al. | |
| 5,595,568 A | 1/1997 | Anderson et al. | |
| 5,616,140 A | 4/1997 | Prescott | |
| 5,618,284 A | 4/1997 | Sand | |
| 5,643,252 A | 7/1997 | Waner et al. | |
| 5,735,844 A | 4/1998 | Anderson et al. | |
| 5,759,200 A | 6/1998 | Azar | |
| 5,810,801 A | 9/1998 | Anderson et al. | |
| 5,817,089 A | 10/1998 | Tankovich et al. | |
| 5,830,208 A | 11/1998 | Muller | |
| 5,830,211 A | 11/1998 | Santana et al. | |
| 5,885,211 A | 3/1999 | Eppstein et al. | |
| 5,897,549 A | 4/1999 | Tankovich | |
| 5,906,609 A * | 5/1999 | Assa et al. | 606/9 |
| 5,925,035 A | 7/1999 | Tankovich | |
| 5,938,657 A * | 8/1999 | Assa et al. | 606/9 |
| 5,957,915 A | 9/1999 | Trost | |
| 5,964,749 A | 10/1999 | Eckhouse et al. | |
| 5,968,033 A | 10/1999 | Fuller et al. | |
| 5,983,900 A | 11/1999 | Clement et al. | |
| 6,015,404 A | 1/2000 | Altshuler et al. | |
| RE36,634 E | 3/2000 | Ghaffari | |
| 6,036,684 A | 3/2000 | Tankovich et al. | |
| 6,050,990 A | 4/2000 | Tankovich et al. | |
| 6,059,820 A | 5/2000 | Baronov | |
| 6,063,108 A | 5/2000 | Salansky et al. | |
| 6,074,382 A * | 6/2000 | Asah et al. | 606/9 |
| 6,083,217 A | 7/2000 | Tankovich | |
| 6,096,029 A | 8/2000 | O'Donnell, Jr. | |
| 6,106,514 A | 8/2000 | O'Donnell, Jr. | |
| RE36,872 E | 9/2000 | Zair | |
| 6,120,497 A | 9/2000 | Anderson et al. | |
| 6,149,644 A | 11/2000 | Xie | |
| 6,152,917 A | 11/2000 | Tankovich | |
| 6,162,211 A | 12/2000 | Tankovich et al. | |
| 6,165,170 A | 12/2000 | Wynne et al. | |
| 6,171,302 B1 | 1/2001 | Talpalriu et al. | |
| 6,190,377 B1 | 2/2001 | Kuzdrall | |
| 6,197,020 B1 | 3/2001 | O'Donnell, Jr. | |
| 6,219,575 B1 | 4/2001 | Nemati | |
| 6,241,753 B1 | 6/2001 | Knowlton | |
| 6,267,771 B1 | 7/2001 | Tankovich et al. | |
| 6,273,884 B1 | 8/2001 | Altshuler et al. | |
| 6,315,772 B1 | 11/2001 | Marchitto et al. | |
| 6,328,733 B1 | 12/2001 | Trost | |
| 6,350,261 B1 | 2/2002 | Domankevitz et al. | |
| 6,375,672 B1 | 4/2002 | Aksan et al. | |
| 6,387,089 B1 | 5/2002 | Kreindel et al. | |
| 6,395,000 B1 | 5/2002 | Mitchell et al. | |
| 6,406,474 B1 | 6/2002 | Neuberger et al. | |
| 6,413,267 B1 | 7/2002 | Dumoulin-White et al. | |
| 6,436,127 B1 | 8/2002 | Anderson et al. | |
| 6,443,946 B2 | 9/2002 | Clement et al. | |
| 6,493,570 B1 * | 12/2002 | Dees et al. | 600/411 |
| 6,508,813 B1 | 1/2003 | Altshuler | |
| 6,511,475 B1 | 1/2003 | Altshuler et al. | |
| 6,514,244 B2 | 2/2003 | Pope et al. | |
| 6,514,278 B1 | 2/2003 | Hibst et al. | |
| 6,517,532 B1 | 2/2003 | Altshuler et al. | |
| 6,529,543 B1 | 3/2003 | Anderson et al. | |
| 6,530,915 B1 | 3/2003 | Eppstein et al. | |
| 6,533,774 B1 * | 3/2003 | Ota | 606/9 |
| 6,533,776 B2 | 3/2003 | Asah et al. | |
| 6,537,270 B1 | 3/2003 | Elbrecht et al. | |
| 6,569,155 B1 | 5/2003 | Connors et al. | |
| 6,569,156 B1 | 5/2003 | Tankovich et al. | |
| 6,572,637 B1 | 6/2003 | Yamazaki et al. | |
| 6,575,963 B1 | 6/2003 | Van Saarloos et al. | |
| 6,579,283 B1 | 6/2003 | Tobinick | |
| 6,600,951 B1 | 7/2003 | Anderson | |
| 6,605,080 B1 | 8/2003 | Altshuler et al. | |
| 6,613,040 B2 | 9/2003 | Tankovich et al. | |
| 6,613,042 B1 | 9/2003 | Tankovich et al. | |
| 6,632,219 B1 | 10/2003 | Baranov et al. | |
| 6,652,512 B2 | 11/2003 | Ota | |
| 6,653,618 B2 | 11/2003 | Zenzie | |
| 6,659,999 B1 | 12/2003 | Anderson et al. | |
| 6,660,000 B2 | 12/2003 | Neuberger et al. | |
| 6,676,654 B1 | 1/2004 | Balle-Petersen et al. | |
| 6,695,835 B2 | 2/2004 | Furuno et al. | |
| 6,723,090 B2 | 4/2004 | Altshuler et al. | |
| 6,733,492 B2 * | 5/2004 | Ota et al. | 606/9 |
| 6,758,845 B1 | 7/2004 | Weckwerth et al. | |
| 6,788,967 B2 | 9/2004 | Ben-Haim et al. | |
| RE38,670 E * | 12/2004 | Asah et al. | 606/9 |
| 6,984,228 B2 * | 1/2006 | Anderson et al. | 606/9 |
| 6,991,644 B2 | 1/2006 | Spooner et al. | |
| 6,997,923 B2 * | 2/2006 | Anderson et al. | 606/9 |
| 2001/0007068 A1 * | 7/2001 | Ota et al. | 606/9 |
| 2002/0002367 A1 | 1/2002 | Tankovich et al. | |
| 2002/0107509 A1 | 8/2002 | Neuberger et al. | |
| 2002/0120256 A1 | 8/2002 | Furuno et al. | |
| 2002/0161357 A1 | 10/2002 | Anderson et al. | |
| 2002/0173782 A1 | 11/2002 | Cense et al. | |
| 2003/0032950 A1 | 2/2003 | Altshuler et al. | |
| 2003/0034959 A1 | 2/2003 | Davis et al. | |
| 2003/0036751 A1 | 2/2003 | Anderson et al. | |
| 2003/0039250 A1 | 2/2003 | Altshuler et al. | |
| 2003/0055414 A1 * | 3/2003 | Altshuler et al. | 606/9 |
| 2003/0109860 A1 | 6/2003 | Black | |
| 2003/0216719 A1 | 11/2003 | Debenedictis et al. | |
| 2004/0015157 A1 | 1/2004 | Connors et al. | |
| 2004/0045948 A1 | 3/2004 | Shalev et al. | |
| 2004/0093042 A1 * | 5/2004 | Altshuler et al. | 607/88 |
| 2004/0100444 A1 | 5/2004 | Park et al. | |
| 2004/0133251 A1 * | 7/2004 | Altshuler et al. | 607/88 |
| 2004/0143247 A1 | 7/2004 | Anderson et al. | |
| 2005/0049582 A1 | 3/2005 | DeBenedictis et al. | |
| 2005/0062720 A1 | 3/2005 | Rotzoll et al. | |
| 2005/0094154 A1 | 5/2005 | Levernier et al. | |
| 2005/0137584 A1 | 6/2005 | Lemchen | |
| 2005/0143719 A1 * | 6/2005 | Sink | 606/9 |
| 2006/0011024 A1 | 1/2006 | Azar et al. | |
| 2006/0116669 A1 * | 6/2006 | Dolleris | 606/17 |

FOREIGN PATENT DOCUMENTS

| | | | |
|---|---|---|---|
| WO | WO 99/11324 A1 | 3/1999 | |
| WO | WO 99/27997 A1 | 6/1999 | |
| WO | WO 01/23032 A2 | 4/2001 | |
| WO | WO 01/26573 A1 | 4/2001 | |
| WO | WO 01/39834 A1 | 6/2001 | |
| WO | WO 2004/037068 A3 | 5/2004 | |
| WO | WO 2004/069325 A2 | 8/2004 | |
| WO | WO 2004/086947 A2 | 10/2004 | |
| WO | WO 2005/016453 A1 | 2/2005 | |

OTHER PUBLICATIONS 6,344,051, Withdrawn.

Andersen, Dan E. et al., "System for the automated photothermal treatment of cutaneous vascular lesions," *Journal of Biomedical Optics* 9(2) (Mar./Apr. 2004), pp. 308-314.

Apfelberg, David B. et al., "Dot or Pointillistic Method for Improvement in Results of Hypertrophic Scarring in the Argon Laser Treatment of Portwine Hemangiomas", *Lasers in Surgery and Medicine*, vol. 6 (1987), pp. 552-558.

Apfelberg, David B., "Intralesional Laser Photocoagulation—Sterioids as an Adjunct to Surgery for Massive Hermangiomas and Vascular Malformations", *Annals of Plastic Surgery*, vol. 35, No. 2 (Aug. 1995), pp. 144-149.

EIMEX Software and Consulting, 4042 Camrose Avenue, Livermore, CA 94550, 2-page paper with synopsis, description, comments, analysis and opinion of Wyman article submitted herewith.

Fujii, Hitoshi et al., "Multispot laser photocoagulation system using a fiber bundle scanner," *Applied Optics*, vol. 21, No. 19, Oct. 1, 1982, pp. 3437-3442.

Manstein, Dieter et al., "Fractional Photothermoysis: A New Concept for Cutaneous Remodeling Using Microscopic Patterns of Thermal Injury," *Lasers in Surgery and Medicine*, vol. 34 (2004), pp. 426-438.

Wyant, J.C., "Rotating Diffraction Grating Laser Beam Scanner", *Applied Optics*, vol. 14, May 1975, pp. 1057-1058.

Wyman, D.R. et al., "A Control Method for a Nonlinear Multivariable System: Application to Interstitial Laser Hyperthermia," *IEEE Transactions on Biomedical Engineering*, vol. 38, No. 9, Sep. 1991, pp. 891-898.

U.S. Appl. No. 60/458,770, filed Mar. 2003, Manstein et al.

International Search Report and Written Opinion, PCT/US05/28095, Jul. 7, 2006, 12 pages.

* cited by examiner

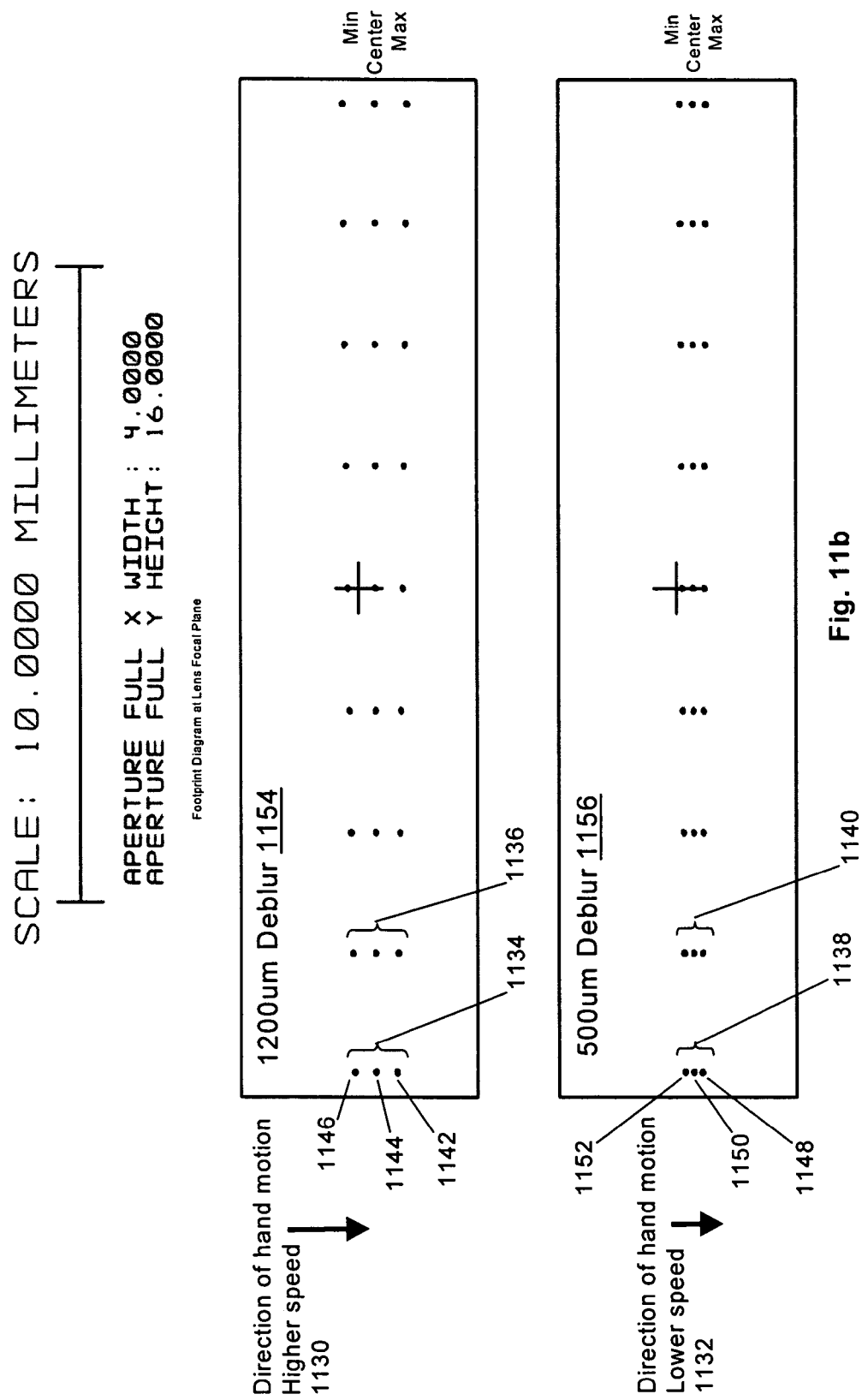

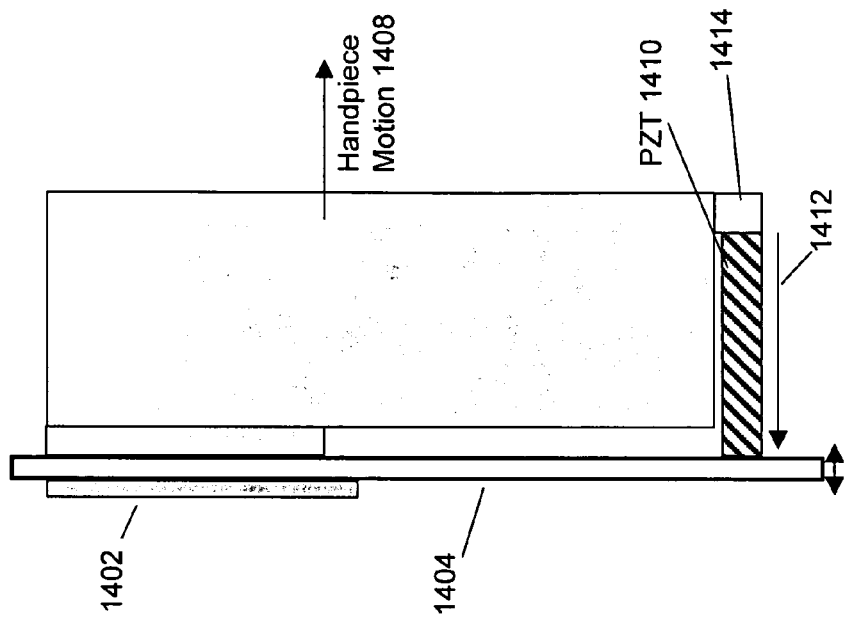
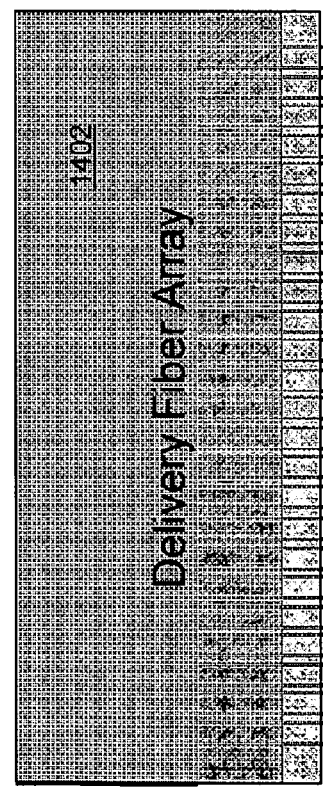
Fig. 14a
Fig. 14b
The PZT Actuator pushes the fiber array to generate the deblurring beam motion

METHOD AND APPARATUS FOR MONITORING AND CONTROLLING LASER-INDUCED TISSUE TREATMENT

CROSS-REFERENCE TO RELATED APPLICATION

This application is a continuation-in-part of U.S. patent application Ser. No. 10/745,761, "Method and Apparatus for Monitoring and Controlling Laser-Induced Tissue Treatment," filed Dec. 23, 2003; and is also a continuation-in-part of U.S. patent application Ser. No. 10/750,790, "High Speed, High Efficiency Optical Pattern Generator Using Rotating Optical Elements," filed Dec. 31, 2003 now U.S. Pat. No. 7,184,184; and also claims priority under 35 U.S.C. § 119(e) to U.S. Provisional Patent Application Ser. No. 60/605,092, "Method and Apparatus for Monitoring and Controlling Laser-Induced Tissue Treatment," filed Aug. 26, 2004. All of the foregoing are incorporated herein by reference.

FIELD OF THE INVENTION

The present invention relates to a method and apparatus for dermatological tissue treatment, and more particularly, to a method and apparatus comprising a combination of a light source, a handpiece, and a means for measurement of the handpiece motion utilized for controlling the tissue treatment.

BACKGROUND OF THE INVENTION

Lasers and other intense light sources are used for various types of tissue treatment, including dermatological tissue treatment. During dermatological tissue treatment utilizing light, a light beam irradiates the skin surface of a patient. Generally, lasers that are used for such treatment operate at a wavelength that is absorbed by one of the natural chromophores in the skin, such as water. In the case of water as the primary chromophore, cellular and interstitial water absorbs light energy and transforms the light energy into thermal energy. The transport of thermal energy in tissues during treatment is a complex process involving conduction, convection, radiation, metabolism, evaporation and phase change that vary with the operational parameters of the light beam. It is essential in such procedures not to damage tissue underlying or surrounding the target tissue area. If the light beam optical operational parameters, such as wavelength, power, the intensity of the light, pulse duration, rate of emission, etc. are properly selected, cellular and interstitial water in the patient's skin is heated causing temperature increases that produce a desired dermatological effect. Conversely, improper selection of the optical operational parameters can result in undertreatment or overtreatment of the tissue. Therefore, it is desirable to accurately control optical operational parameters used in the treatment so that the light is delivered to the tissue with the proper fluence and in a uniform, controllable manner. A variety of devices have been proposed that intelligently control laser beam power, intensity, duration, etc. However, as will be discussed in greater detail below, application of these devices have significant disadvantages.

Known devices for dermatological tissue treatment include a hand-held delivery apparatus, sometimes referred to as a handpiece. A handpiece is the preferred means by which physicians apply treatment to tissue. During treatment, the handpiece emitting light is moved by a physician's hand along the tissue to be treated. Treatment level from such a device is typically set in advance by manually selecting the light beam operational parameters. The operational parameters, which for example include power level, energy, pulsation rate, temperature, light intensity, and current, determine the degree of treatment of the entire treatment process.

One disadvantage of some of the existing handpiece apparatuses is that they require strict precision in positioning of the handpiece and application of controlled movement in order to stay within limits of safe, uniform and efficacious treatment. Theoretically, strict precision can be achieved with a high degree of skill, attention and dexterity from the treating physician. In a real procedure, however, manual application and control of the handpiece can easily result in non-uniformity of treatment due to imprecise or involuntary movements of the human hand and/or uneven tissue surfaces. This often results in either some areas of the targeted tissue being under-treated, or causes some areas to be over-treated.

A typical approach of known handpieces is to produce a macroscopic, pulsed treatment beam that is manually moved from one area of the skin to another in a patchwork like manner in order to treat a larger region of skin tissue. Such an approach has the disadvantage of producing artifacts and sharp boundaries associated with the inaccurate positioning of the individual treatments with respect to the treated skin surface.

Another disadvantage of known handpieces is that, as discussed- above, the laser operational parameters defining the selected level of treatment are typically pre-set once for the entire course of treatment. The individual tissue properties of each patient are factored-in based on a preliminary tissue assessment prior to the treatment and the treatment can proceed using the predetermined operational parameters.

For example, some existing handpiece apparatuses provide feedback indicating to the physician the rate of the handpiece movement which allows the physician to adjust the treatment speed. But this handpiece apparatus requires the physician to treat at a pre-selected rate of motion. The disadvantage of this apparatus is that it restricts the physician to a single treatment speed. In large flat areas, such as the cheek, it is desirable to treat at a high speed. In highly contoured areas, such as the lip, it is desirable to treat at a lower speed. Restricting the physician to a pre-selected rate of motion limits the flexibility of the physician when treating regions, such as the face, that include both large flat areas and highly contoured areas that are in close proximity. Additionally, if the speed of the handpiece changes during the treatment procedure, the apparatus does not provide for automatic adjustment of its operational parameters to compensate for the changed rate of movement, leading to uneven treatment.

The application of robotic means used in the field of dermatological or cosmetic surgery could overcome the limitation of human imprecision. However, one disadvantage of typical conventional robotic apparatuses is that they lack the necessary direction and judgment in treatment that a physician provides. Although robotics is precise, it is not typically intelligent enough to make complex choices or react to unforeseen circumstances during treatment. Additionally, robots deprive a physician of discretion in an aesthetic sense.

Another disadvantage of the typical conventional robotic apparatus is that the full treatment may require complete immobilization of the patient. Alternatively, a sophisticated image stabilization system must be employed to compensate for patient's movement. It is still another disadvantage of such robotic apparatuses that they are bulky and cannot be easily moved into treatment positions in relation to the areas allowing little room for movement. Rather, a tissue surface to be treated has to be brought into a specific position in relation to the apparatus before treatment can take place.

The present invention provides a method and apparatus which significantly reduce the problems associated with the existing laser-induced handpieces apparatuses and robotics.

SUMMARY OF THE INVENTION

The present invention provides improved methods and apparatus for controlling light-induced tissue treatment that overcome many of the shortcomings of the prior art. The ways in which the present invention addresses the drawbacks of the now-known techniques for dermatological tissue treatment will be described in greater detail herein. In accordance with various aspects of the present invention, the invention provides for improved, real-time control of the light beam operational parameters which enables greater safety, efficiency, uniformity and continuity of the treatment process.

It is an object of the present invention-to provide a more precise and efficient technique for uninterrupted hand-delivered tissue treatment by a freely movable handpiece augmented by a feedback controlling means for improved overall quality of treatment.

It is another object of the present invention to monitor and automatically control in substantially real-time or quasi-real time operational parameters of the treatment beam(s) in response to detected variations in the position and/or movement of the handpiece, whereby optimum treatment conditions can be achieved throughout the treatment irrespective of these variations.

It is a further object of the present invention to provide a method and apparatus for hand-delivered tissue treatment that in real-time adjusts output optics of the handpiece in response to variations in the handpiece positional parameters to simultaneously deliver the light beam in a controlled discontinuous pattern to a plurality of discrete treatment zones with a minimum collateral damage to the intentionally untreated tissue and without blurring or distorting the intended shape and/or dimension of the discrete treatment zones.

It is still a further object of the present invention to provide a method and apparatus for hand-delivered tissue treatment that is adapted to provide uniform light beam fluence and patterns irrespective of the individual target tissue properties and the handpiece velocity.

These and other objects and features will be apparent from the following description of the present invention contained herein.

In one aspect, the invention is directed to an apparatus for controlled tissue treatment. The apparatus comprises a source of a light beam. The light beam has a plurality of controllable operational parameters for a pre-selected tissue treatment at a pre-determined dosage. Further, the apparatus comprises a movable handpiece adapted to receive the light beam for delivering to an area in tissue to be treated. The movement of the handpiece is defined by a plurality of variable positional parameters, such that variation in at least one positional parameter changes the dosage of the pre-selected tissue treatment. The apparatus has a detector for detecting and measuring in real-time the variation in at least one of the handpiece positional parameters. The detector is coupled to a controller for automatically controlling in real-time the light beam operational parameters to affect a new treatment rate in response to the variation in at least one positional parameter whereby the pre-selected tissue treatment can continue at a pre-determined dosage.

Implementations of the invention may include one or more of the following features.

The controller may comprise a processor for receiving signals indicative of the variations in the positional parameters and calculating in real-time the desired operational parameters as a function of positional parameters. Alternatively, the processor may comprise storage of coherent datasets of positional parameters and corresponding operational parameters for continuous mapping of operational parameters as a function of positional parameters.

The controller may further comprise an interface unit for selecting initial operational parameters; for receiving from the detector, processing and forwarding to the processor signals indicative of the variations in positional parameters; for receiving a new set of operational parameters from the processor; and for modifying in real-time operational modes of one or more system components based on the new set of operational parameters to effectuate a new treatment rate.

The detector may include an image-processing element for determining variations in two-dimensional or three-dimensional movement of the handpiece with high precision. The detector may be an accelerometer, an optical detector array, a capacitive sensor array or a profilometer.

The handpiece may include a refractive or diffractive focusing element, which enables the delivery of the light beam from the handpiece to the target area in a pre-selected microscopic pattern. The system may also include various delivery mechanisms for delivering the beam, such delivery mechanisms may include scanning mechanisms, galvanometers, piezoelectric elements, moving mirrors, diffractive elements, holographic elements, MEMS, nanotechnology, acousto-optic elements and/or electro-optic elements.

The controller may comprise a means for sound, vibration, or visual feedback to help a physician maintain handpiece movement in a predetermined range.

In another aspect, the invention is directed to a method for uniform tissue treatment using the handpiece apparatus of this invention. The handpiece emits a light treatment beam having a plurality of operational parameters for a pre-selected tissue treatment at a pre-determined dosage. The handpiece is moved by an operator's hand to apply the treatment to a target tissue area at variable positional parameters such that upon variation in at least one of the handpiece positional parameters, the dosage of the tissue treatment changes. Variations in at least one variable positional parameter are continuously or substantially continuously detected and measured in real-time by a detector. A set of desired operational parameters is determined by a processor based on the variations in the positional parameters, and control information is outputted to a controller. Operational parameters are adjusted in real-time in response to the control information from the processor to effect a new treatment rate. The tissue treatment continues at the new treatment rate, whereby the pre-determined treatment dosage is automatically maintained.

BRIEF DESCRIPTION OF THE DRAWINGS

A more complete understanding of the present invention may be derived by referring to the detailed description and claims, considered in connection with the figures, wherein like reference numbers refer to similar elements throughout the figures.

FIGS. 11a and 11b show an example of an embodiment of the present invention having a two-axis galvanometer scanning system for de-blurring.

FIGS. 14a and 14b show an example of an embodiment of the present invention having a fiber array and a piezoelectric flex-induced de-blurring actuator.

DETAILED DESCRIPTION OF EXEMPLARY EMBODIMENTS

Figure 1:
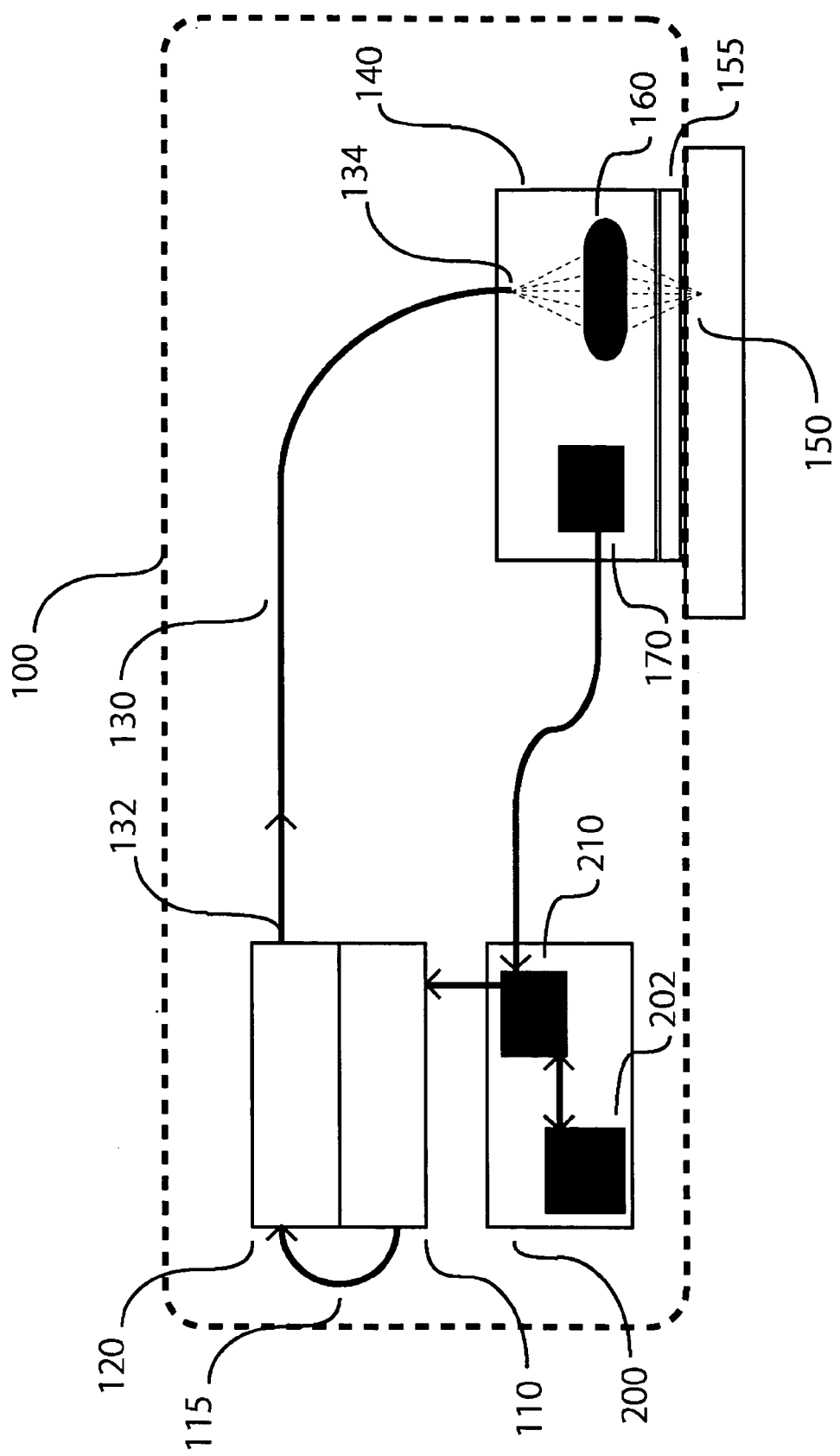
FIG. 1 is a diagrammatic view of an apparatus according to the invention showing feedback control of the laser power for controlled tissue treatment.

FIG. 1 illustrates a laser apparatus for controlled tissue treatment 100 in accordance with the present invention. Tissue may include skin tissue as well as other tissues throughout a living body. Various embodiments and examples described herein may refer to skin treatment, but it is understood by those skilled in the art that other tissues can be treated similarly.

In accordance with the exemplary embodiment shown in FIG. 1, apparatus 100 comprises power source 110 that energizes light emitter 120 for emission of a light beam via an electrical or optical connection 115; optical fiber 130 for transmission of the light beam; movable handpiece 140 with optical element 160 coupled to optical fiber 130 for emission of the light beam towards target area 150; detector 170 for detecting variations in positional parameters of handpiece 140; and controller 200 for controlling operational parameters of the light beam emitted towards target area 150 in response to the detected variations in the handpiece positional parameters. Light is typically passed through an optically transparent window 155 that may be flat or curved. The connection 115 may consist of simply a region through which an optical beam is passed. Controller 200 may comprise processor 202 for calculating new operational parameters and interface unit 210 for selecting and adjusting operational parameters of apparatus 100. The controller 200 may control operational parameters by adjusting parameters in at least one of the following: power source 110, light emitter 120, and optical element 160. For clarity, only one of these configurations is illustrated.

Light emitter 120 of apparatus 100 may be any optical power source or may simply emit optical power that is created by power source 110. Light emitter 120 may be implemented, at least in part, using one or more light power sources. For certain applications, light emitter 120 may desirably include multiple light power sources arranged in an array, such as a one-dimensional array or two-dimensional array. It is preferred that the light power source utilized in the present invention is a laser. Suitable lasers according to the invention may include noble gas lasers (e.g., argon lasers, helium-neon lasers, etc.), diode lasers, fiber lasers, and tunable dye lasers. However, it must be understood that the selection of a particular laser for the tissue treatment apparatus 100 is dependent on the type of the dermatological treatment selected for a particular application. Light emitter 120 of the present invention is adapted to produce optical power between about 1 W and about 100 W, preferably about 10 W.

Light emitter 120 emits one or more optical beams. In laser-induced tissue treatment, each optical beam may be characterized by a particular set of optical operational parameters that are selected to produce a desired dermatological effect on target area 150. Operational parameters of the light beam (i.e. optical operational parameters) may include optical fluence, power, pulsation rate, duty cycle, light intensity, timing of pulse initiation, pulse duration, and wavelength.

Light emitter 120 is preferably capable of generating light at wavelengths with high absorption in water. Cellular water absorbs light energy and transforms the light energy into heat. Preferably, wavelengths larger than 190 nm, such as wavelengths in the range from 190 nm to 10600 nm, preferably from 700 nm to 3000 nm, and most preferably about 1550 nm are used in the apparatus 100. Desirably, light emitter 120 is an erbium-based fiber laser designed for about 1550 nm range operation. Light emitter 120 may be capable of providing one wavelength or a range of wavelengths or may be tunable across a range of wavelengths. One or more light emitters 120 may be powered by power source 110 to produce a variety of different wavelengths or wavelength ranges used in dermatological treatment. Light emitter 120 may be adapted to selectively produce pulses of laser light at a frequency of between 0 to about 50,000 pulses per second and preferably 0 to about 1,000 pulses per second. Preferably, light emitter 120 emits a beam having pulse energy per treatment spot of about 1 mJ to about 1000 mJ, more preferably in a range between about 10 mJ and about 30 mJ, each pulse having a pulse duration per treatment spot between about 0.1 ms and about 30 ms, more preferably about 1 ms.

Power source 110 and light emitter 120 of the present invention can be used, for example, for non-ablative coagulation of a dermal layer of the target area 150. Typically, for this purpose, an optical fluence incident to target tissue area 150 greater than about 5 J/cm$^2$, such as an optical fluence in the range from about 10 J/cm$^2$ to about 1000 J/cm$^2$, is adequate for coagulating tissue. Generally, the optical fluence is adapted to the wavelength and the tissue to be treated. If various dermatological effects are desired, the power source 110 and light emitter 120 may be selected with the capacity to produce optical operational parameters suitable for other types of tissue treatment. For example, if ablation of an epidermal layer of the target area 150 is desired, the power source 110 and the light emitter 120 may be used with the capability to emit a light beam with a wavelength of about 2940 nm and optical fluence higher than 10 J/cm$^2$.

Optical fiber 130 may be any optical apparatus suitable for transmission of light emitted from light emitter 120. Fiber 130 may be constructed of a material that allows for free manipulation of the handpiece 140 and for repeated bending in order to direct the light beam from emitter 120 to various portions of target area 150. Preferably, optical fiber 130 is an SMF28 fiber manufactured by Corning, Inc. located in Corning, N.Y. Fiber 130 may have beam-inlet end 132 that is aligned with the light beam emitted from light emitter 120 so that the light beam is coupled into optical fiber 130, and beam-outlet end 134 for emission of the transmitted light beam to handpiece 140. More than one fiber may be used to transmit the light beam from emitter 120 to handpiece 140. Preferably, two fibers 130 are employed to deliver light emitted from emitter 120 to handpiece 140. Alternatively, other optical delivery mechanisms 130, e.g., mirrors or waveguides may be used to guide the light beam from the light emitter 120 to the proximal end of handpiece 140.

Figure 2:
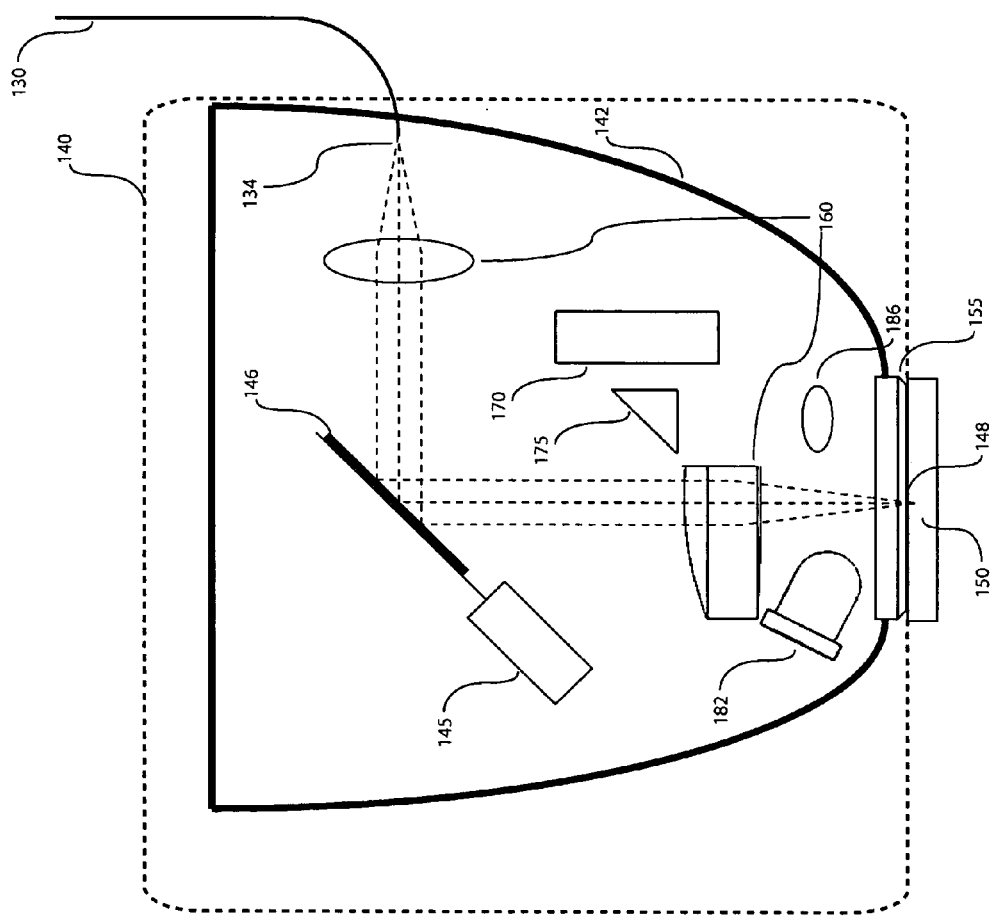
FIG. 2 is a side view of a handpiece according to this invention including a detector and an optical element.

Referring to FIG. 2, the housing 142 of handpiece 140 is generally a single-piece unit adapted for convenient holding by a human hand during the delivery of dermatological treatment. Shape of housing 142 of the handpiece 140 provides for a wide range of motion to manipulate the handpiece during treatment. Housing 142 may be made out of a light plastic, such as Kydex and may hold optics and electronics used for dermatological tissue treatment. Housing 142 may be connected to fibers 130 near the beam-outlet ends 134 and may contain a structure that allows the light beam to be guided through housing 142 and to be emitted from handpiece output 148 at the distal end of the housing, so that the light beam can propagate towards target area 150. For the most efficient treatment, it is preferred to direct and point the light beam emitted from output 148 at a substantially right angle to the surface of output 148.

Handpiece 140 may further include optical elements 160 that are optically coupled to fibers 130. Optical elements 160 direct optical energy from fibers 130 to target tissue area 150. In the preferred embodiment, optical elements 160 direct optical energy to target area 150 by focusing or collimating the light beams emitted from fibers 130 to one or more treatment zones within target area 150. Optical elements 160 may be implemented using one or more optical elements, such as mirrors, optical lenses or optical windows. Typically, for non-ablative treatment, the swath width of target area 150 is pre-selected at about 0.5 cm to 2.0 cm.

Optical elements 160 may be configured to allow for control of the microscopic treatment patterns and density of the treatment zones. As will be discussed in greater detail below, substantially uniform pre-selected pattern and density of the treatment zones across the entire treated tissue area may be achieved by controlling optical elements 160. Typical treatment patterns include: discrete treatment zone spot diameters (i.e. at the 1/e location or the full width half maximum (FWHM) location of the beam, typically at the surface of the tissue) of less than about 500 microns, and preferably less than about 250 microns, and more preferably less than about 100 microns; treatment densities of between about 100 and 2000 treatment zones per square centimeter per handpiece pass over a given tissue area; separations between discrete treatment zones of greater than about 75 microns, with untreated and/or undamaged tissue between discrete treatment zones; and substantially cylindrical (or ellipsoid) treatment zones with the axis of the cylinder (or the major axis of the ellipsoid) typically perpendicular to the surface of the tissue. Embodiments of the present invention may produce other treatment patterns and dimensions as disclosed, for example, in co-pending patent application entitled "Method and Apparatus for Fractional Photo Therapy of Skin", filed on Jul. 9, 2004, and incorporated herein by reference.

Handpiece 140 may further comprise deflector 146. Deflector 146 may be an optical component suitable for deflecting the light beam of the wavelength pre-selected for the treatment, such as mirrors, prisms, grids, diffractive optical elements, such as holograms, etc. Deflector 146 may be operationally coupled to optical element 160 to modify the light beam emitted from optical element 160. Preferably, deflector 146 is movably mounted within housing 142 for displacement by actuator 145 in response to a controlling signal. Actuator 145 may operate to adjust the position of deflector 146 to a position corresponding to the desired treatment intensity and pattern. Actuator 145 may be controlled in real-time by controller 200 to modify the light beam so that the microscopic treatment is delivered from handpiece 140 in a uniform manner across target area 150, whether the pattern is constant and continuous or discontinuous. In some embodiments, optical elements 160 and actuator 145 are part of the delivery system. Delivery parameters for such embodiments may include, for example, treatment beam size and shape, treatment beam angle of exit from the handpiece, numerical aperture, focal distance, scanner speed, scan direction, treatment pattern, etc. Discrete treatment zone dimensions and the pattern of discrete treatment zones in the treatment area for a given treatment are typically defined in part by a combination of optical operational parameters and delivery parameters used in the optical system and delivery system of a given embodiment.

Figure 3:
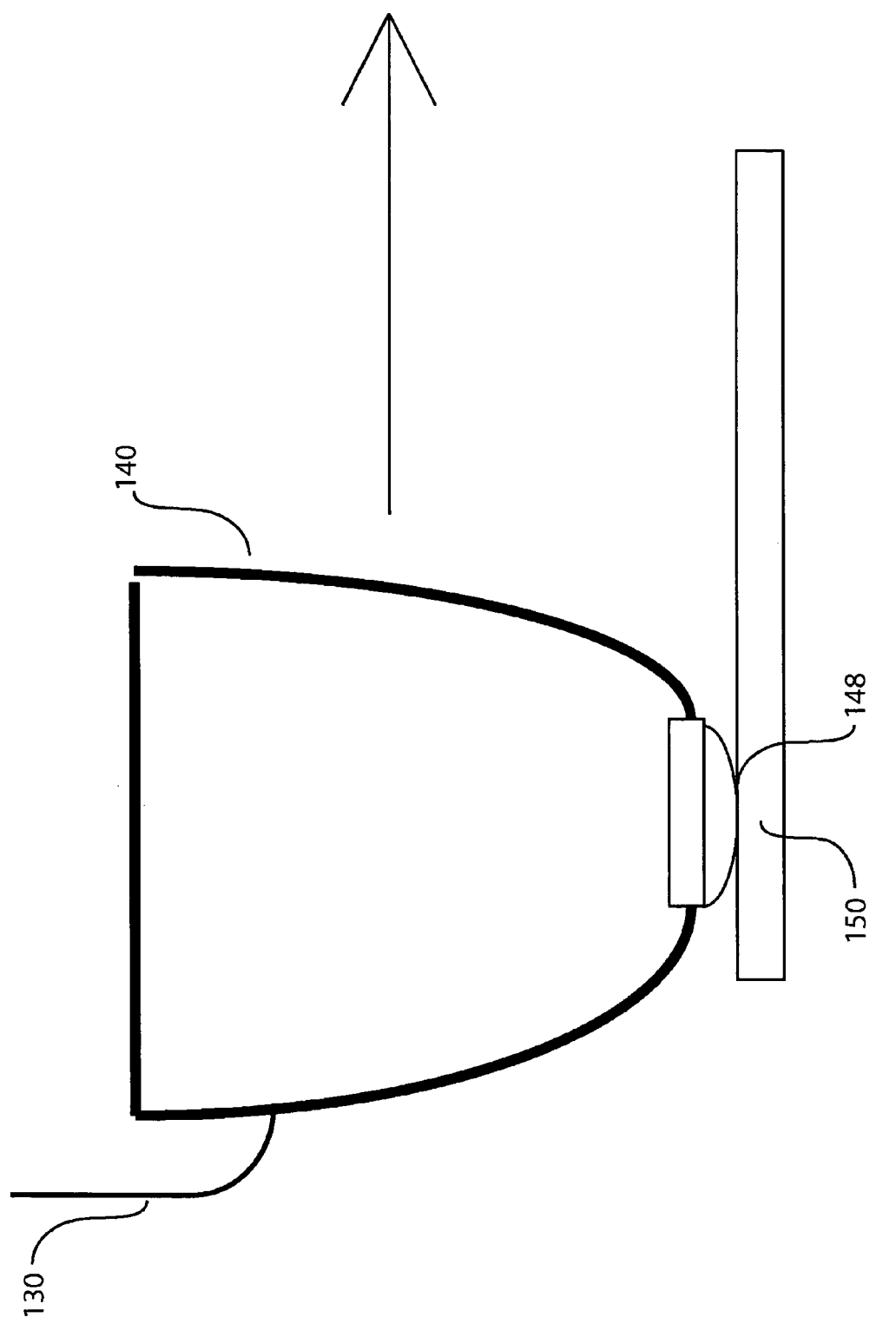
FIG. 3 is a simplified cross-sectional view schematically showing variation of a handpiece positional parameter relative to the target tissue.

Referring to FIG. 3, to achieve the best treatment result, handpiece 140 preferably is positioned at a predetermined distance from target area 150 calculated to focus the light beams in a desired pattern. Specifically, a light beam emitted from fiber 130 is transmitted through the optics of handpiece 140 and focused by optical element 160. The handpiece is positioned at the distance from target area 150 where the light beam from handpiece output 148 is focused at the desired depth in the target area 150. Additionally, the handpiece preferably is moved at a substantially constant or variable velocity of approximately between about 0.5 cm/s and about 10 cm/s, and more preferably between about 2 cm/s and about 6 cm/s, and held in a position that allows the light beam to propagate to the target area at a substantially right angle.

If, during the treatment, the positional parameters of the moving handpiece, e.g., the distance, velocity, and angle of the handpiece relative to the target area are varied, the pre-selected treatment dosage is maintained by the feedback described in this invention. By way of example, the desired dosage for the non-ablative treatment would be maintained at the level of between about 5 J/cm$^2$ and about 2000 J/cm$^2$, preferably between about 150 J/cm$^2$ and about 1000 J/cm$^2$. When the positional parameters vary, the dosage, density, and pattern of the delivered treatment can be preserved at the pre-selected level. Preservation of the pre-selected treatment parameters is accomplished by adjustment of the operational parameters of apparatus 100 by the controller 200.

Specifically, a change in the angle of the handpiece 140 relative to the target area 150 may have a significant effect on the treatment dosage because it changes the angle at which the light beam propagates towards the target area and may affect the depth of optical penetration of the treatment light beam which may affect the treatment level. The change in the treatment level may be substantially compensated for by adjusting the optical power in the light beam, possibly in combination with changes in temperature of the handpiece output window 155. For example, the handpiece output window could be heated above the temperature of the skin. If the output window is then placed in contact with the target area 150, then it would heat the skin and would thus reduce the amount of optical energy that would be required to heat the skin to the desired treatment temperature.

In another example, the dosage of the treatment applied to the target area 150 varies inversely to variations in the physician's hand speed. When the velocity of the beam relative to the target area increases during treatment, the dosage of the delivered treatment decreases, and vice versa. Thus, the imprecision of manual movement of the handpiece results in undesirable changes in the dosage that destroys treatment uniformity and adversely affects safety and efficacy of the treatment. Some embodiments of the present invention allow the controller to compensate for this change in treatment uniformity by adjusting the optical power or other optical operational parameters in the light beam, and/or by altering the delivery system parameters (e.g., scan speeds, beam shape and size, exit angle, etc.). Compensating for changes in handpiece velocity may include avoiding the blurring of treatment zones caused by the movement. Such "de-blurring" is described in greater detail in various embodiments below.

Referring to FIG. 4, the graphs exhibit examples of correlations between handpiece positional parameters, e.g., velocity, distance, and position relative to the target area, and the resulting changes in the treatment rate.

Figure 4A:
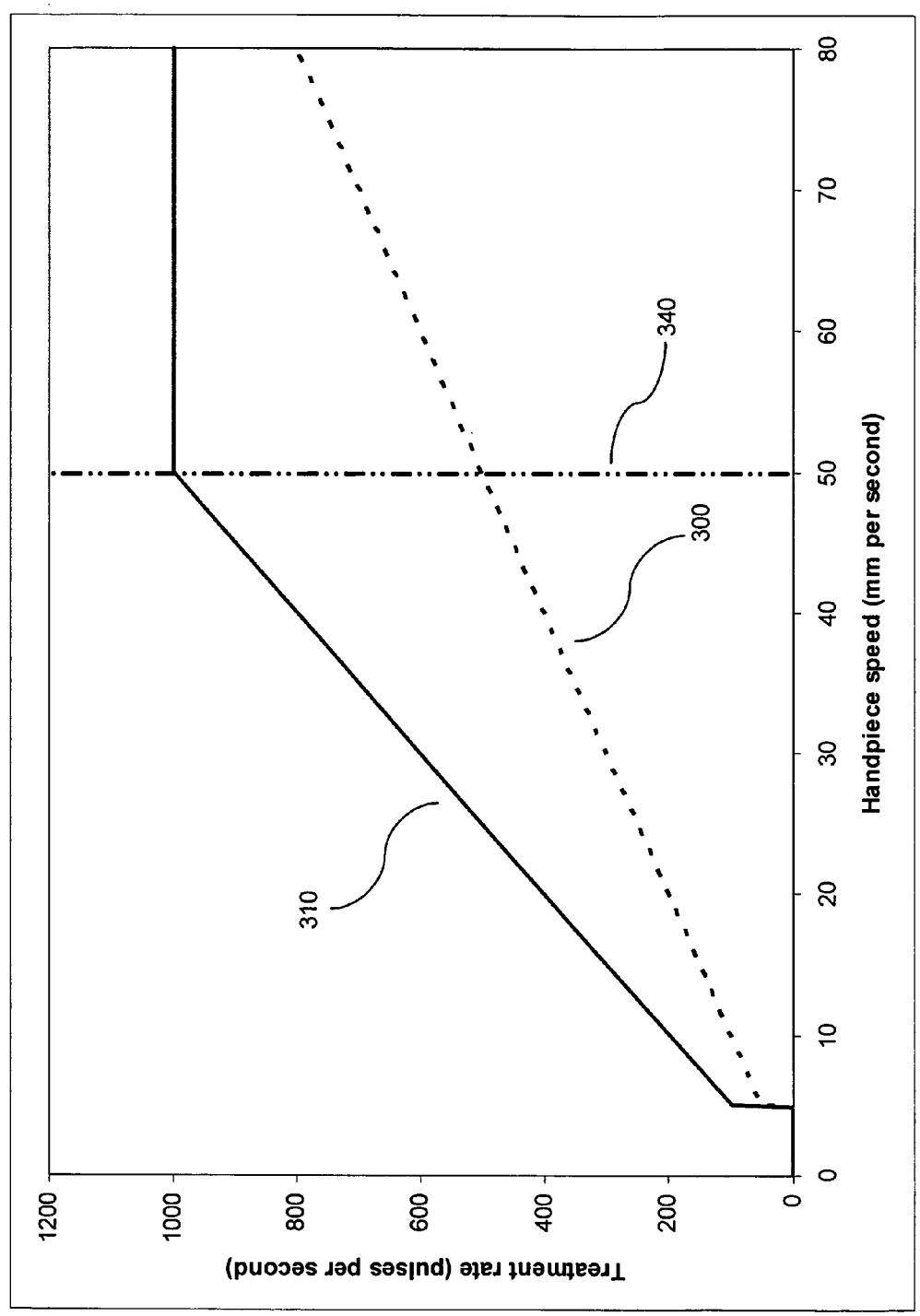
FIGS. 4A-4B are graphs showing correlation between a measured positional parameter and a corresponding set of desired operational parameters for a pulsed light emitter that maintains a preselected treatment dosage.

FIG. 4A illustrates the treatment resulting from apparatus 100 when the light emitter 120 emits light as a pulsed light beam. In this apparatus, the treatment dosage is proportional to the number of pulses per linear mm of treatment. To maintain a constant treatment dosage, the number of pulses should be proportional to the handpiece speed relative to the target area 150 as the handpiece moves parallel to the surface of the target area. The lower curve 300 shows a treatment dosage of 10 pulses per linear mm when the handpiece speed is between 5 and 80 mm/s. For handpiece speeds lower than 5 mm/s, the number of pulses per linear mm can be reduced to zero as a safety feature that prevents noise in the detection circuit from causing a large percentage change in the treatment dosage. The upper curve 310 shows a treatment dosage of 20 pulses per linear mm when the handpiece speed is between 5 and 50 mm/s.

Figure 4B:
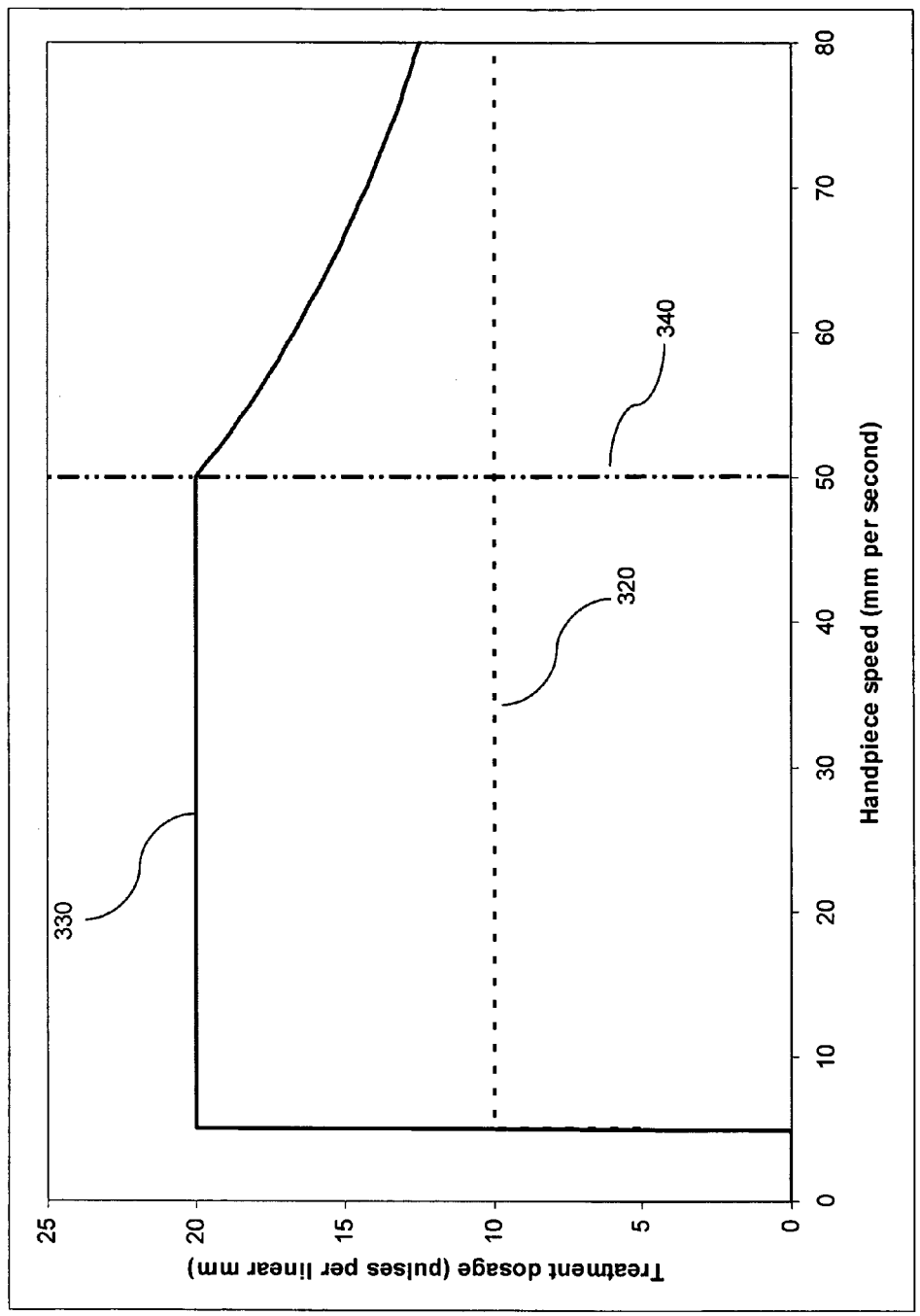

The relationship between handpiece speed and treatment dosage is shown in FIG. 4B. In FIG. 4B, the lower treatment dosage response curve 320 corresponds to the treatment dosage that results from treating according to the treatment parameters specified by the lower curve 300 in FIG. 4A. Similarly, in FIG. 4B, the upper treatment dosage response curve 330 corresponds to the treatment density that results from treating according to the treatment parameters specified by the upper curve 310 in FIG. 4A.

Referring to FIGS. 4A and 4B, the graphs represent a light emitter 120 that cannot emit enough light power to allow the pre-selected treatment dosage to be maintained for handpiece speeds above 50 mm/s at a dosage of 20 pulses per linear mm. The maximum speed 340 for the handpiece may be defined as the limit above which the pre-selected treatment dosage parameters can not be maintained. Referring to FIGS. 4A and 4B, 50 mm/s would be the maximum speed 340 for pre-selected treatment dosages ranging from 0 to 20 pulses per linear mm.

Figure 5A:
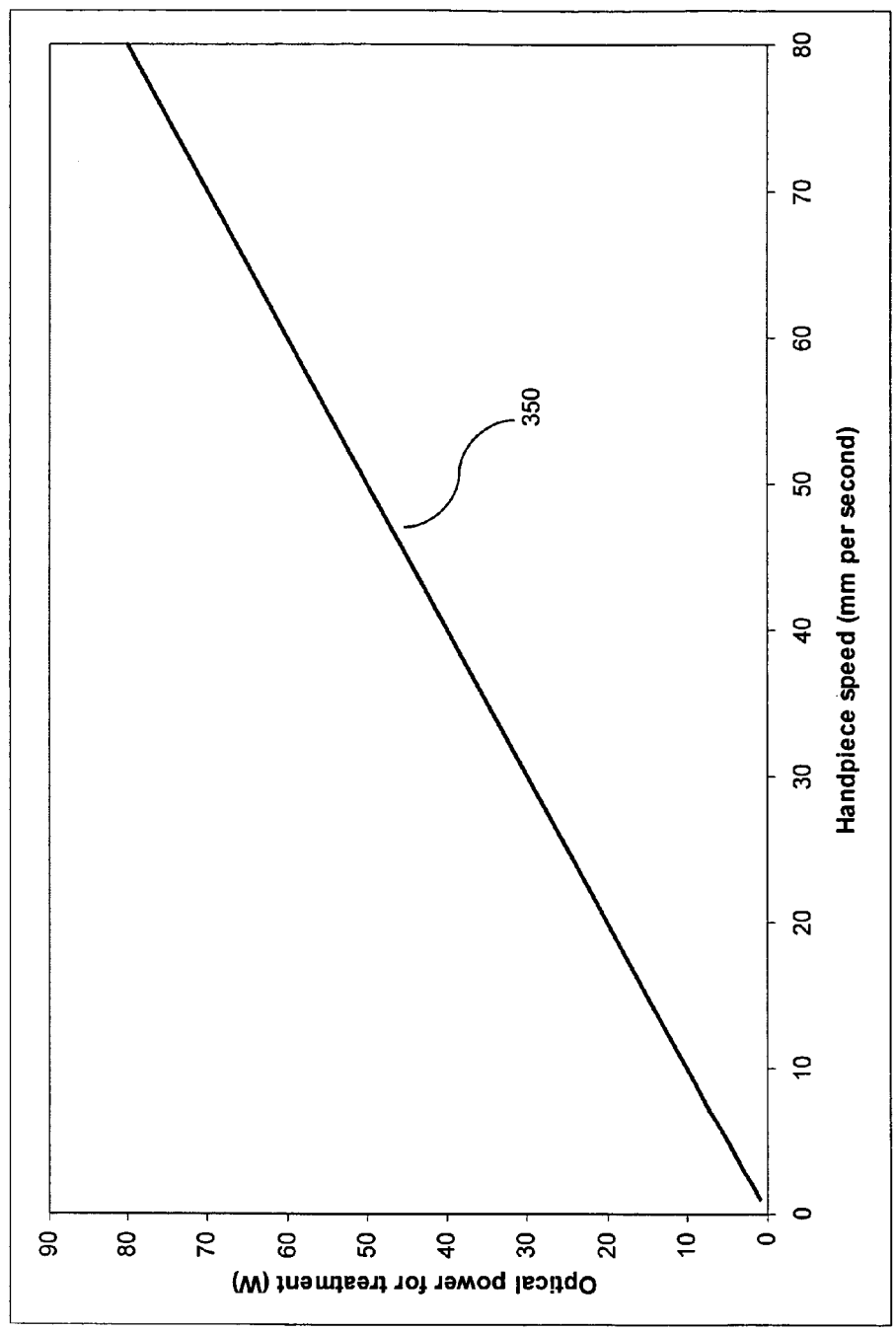
FIGS. 5A-5B are graphs showing correlation between a measured positional parameter and a corresponding set of desired operational parameters for a continuous wave (CW) light emitter that maintains a preselected treatment dosage.

FIG. 5A illustrates the treatment resulting from apparatus 100 when the light emitter 120 emits light as a continuous wave (CW) light beam. In this apparatus, the treatment dosage is proportional to the optical energy from the light beam that is deposited in the target area 150 per linear mm of treatment. To maintain a constant treatment dosage, the light beam energy emitted from light emitter 120 should be proportional to the handpiece speed relative to the target area 150 as the handpiece moves parallel to the surface of the target area. The CW treatment rate curve 350 shows a treatment dosage of 1 J per linear mm when the handpiece speed is between 1 and 80 mm/s. For handpiece speeds lower than 1 mm/s, the number of spots per linear mm can be reduced to zero as a safety feature that prevents noise in the detection circuit from causing a large percentage change in the treatment dosage.

Figure 5B:
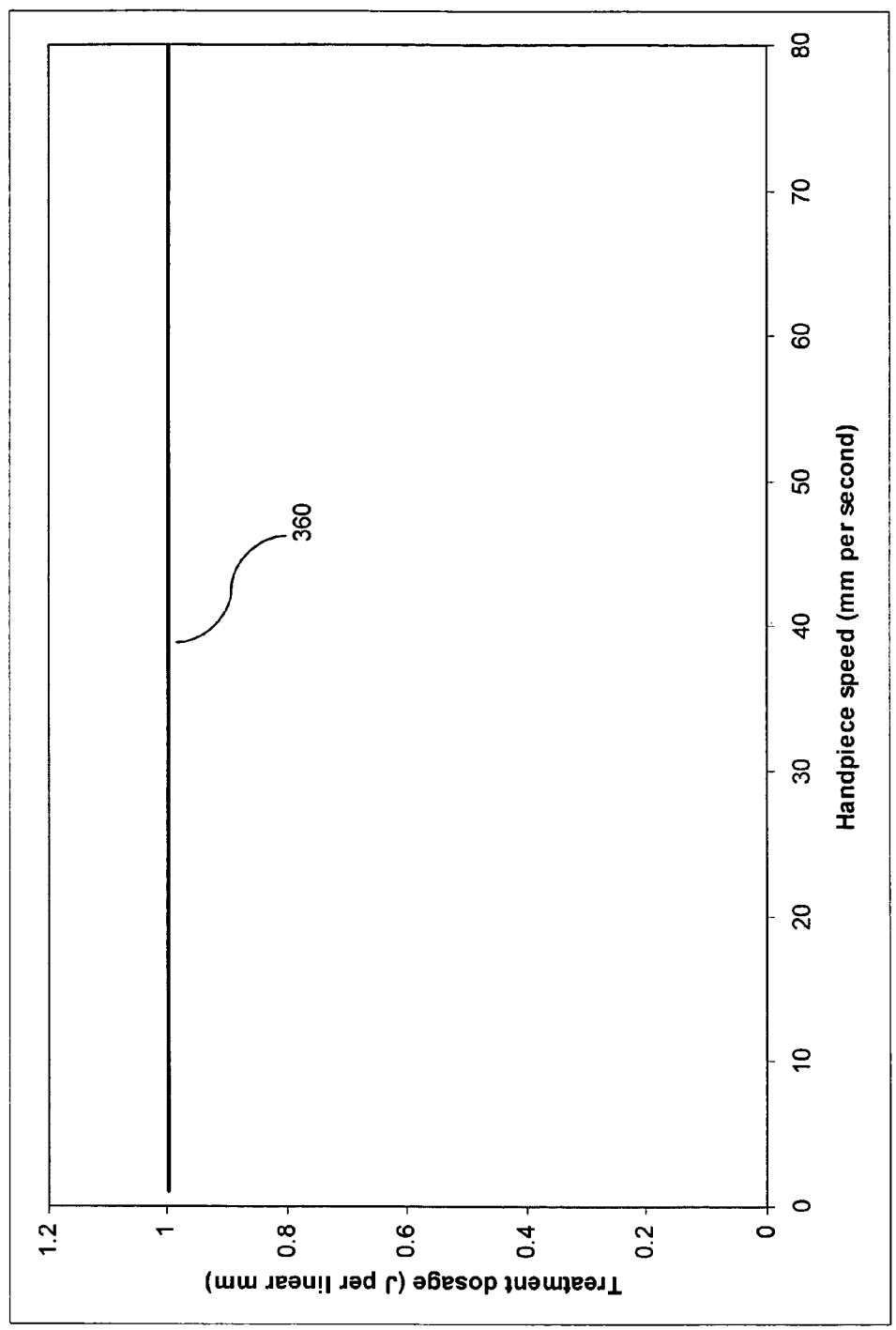

The relationship between handpiece speed and treatment dosage is shown in FIG. 5B. In FIG. 5B, CW treatment dosage response curve 360 corresponds to the treatment dosage that results from treating according to the treatment parameters specified by the CW treatment rate curve 350 in FIG. 5A. The maximum speed 340 is not shown on the graph in FIG. 5A because the maximum speed is greater than or equal to the maximum handpiece speed described by the graph in FIGS. 5A and 5B range of handpiece speeds.

Thus, under both modes of operation exhibited in FIGS. 4A and 5A, the uniformity of tissue treatment dose can be preserved by the appropriate choice of operational parameters for apparatus 100 based on the changes in the handpiece positional parameters when the handpiece speed is below the maximum speed 340.

Figure 6:
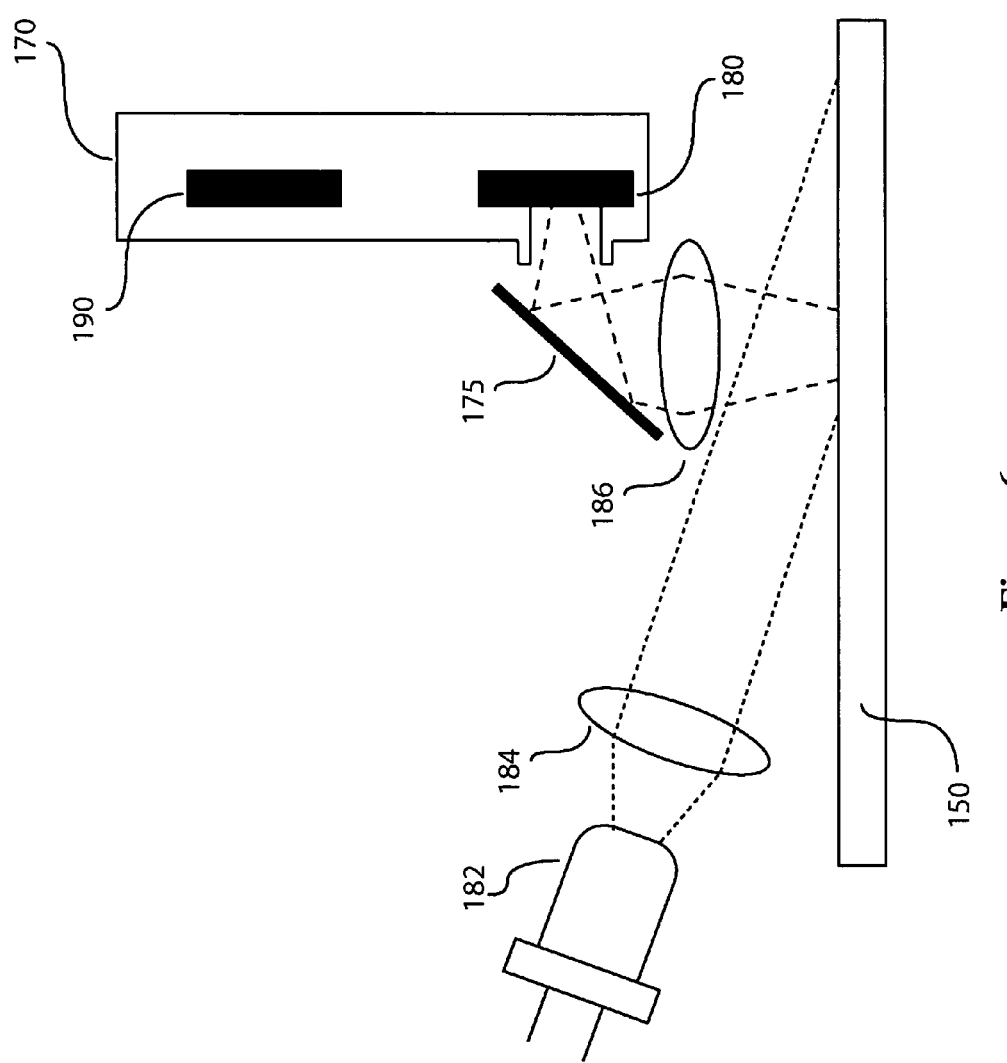
FIG. 6 shows a detector of the handpiece shown in FIG. 2 in sensing mode in greater detail.
Figure 7:
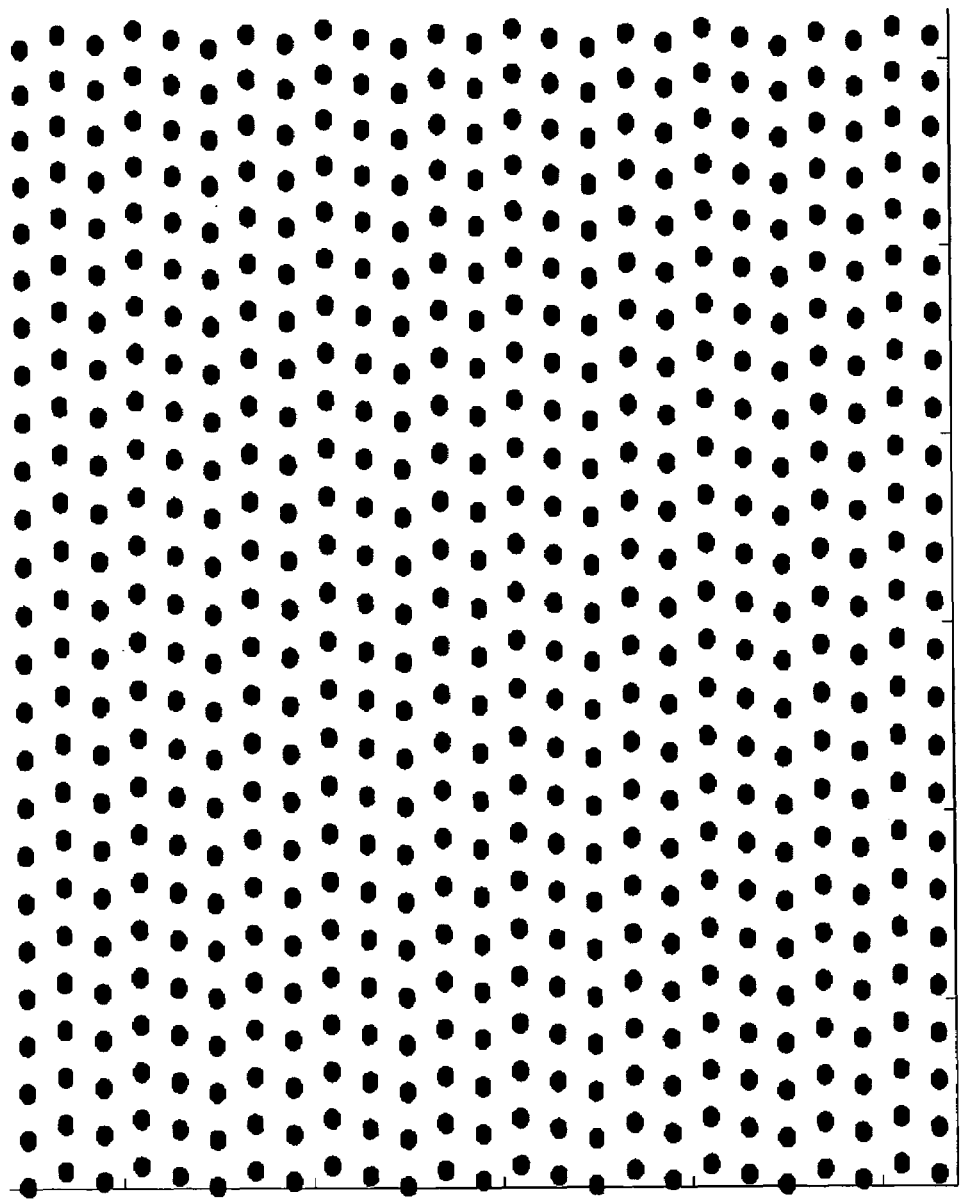
FIG. 7 shows a simulation of an area treated by the invention at a pre-selected density of discrete treatment zones with continuous, controlled in real-time, pattern.

Referring to FIGS. 1 and 6, handpiece 140 advantageously includes detector 170 for detecting variations in the positional parameters of handpiece 140. Detector 170 may comprise an image acquiring sensor 180 for repeatedly capturing images of target area 150 and image processing device 190 for analyzing in real-time varying positional parameters of the moving handpiece 140.

Sensor 180 may be an optical navigation device that allows quantitative measurement of the movement of handpiece 140. The basic operating principle of the optical navigation technique is shown in FIG. 6. Light-emitting diode 182 illuminates the surface of the tissue underneath handpiece 140. The light is converged by means of converging lens 184 on the treated surface to be reflected off the microscopic textural features in the target area 150. The converged beam of light scattered from the surface is then refocused by converging lens 186 to form an image on position sensor 180. Sensor 180 continuously takes pictures of the points in the treated area at high speed as handpiece 140 moves. The image capturing rate of sensor 180 is sufficiently high to allow sequential pictures to overlap. Sequential images from the sensor 180 are sent to image processing device 190. The optical path of sensor 180 between the target area and the converging lens 186 may include an optically transparent window 155.

Image processing device 190 may be a programmable digital computer that uses optical navigation engine for analyzing the sequential images captured by sensor 180.

Image processing device 190 can be designed to use an image-processing algorithm of optical navigation engine to identify the common features between the images. Difference between two sequential images corresponds to changes in the position, velocity and distance of handpiece 140 relative to target area 150 at two sequential points in time. Preferably, controller 200 stores a set of rules for determining conditions suitable for dermatological treatment based on the set of one or more positional parameters measured by detector 170. The set of rules may be stored in a file associated with a particular type of treatment or in a file associated with the treatment designed for a particular patient, so that different patients can have different treatment conditions. The rules may include a rule expressed as a variable operational parameter calculated based on one or more variations in measurements of positional parameters. The rules may also include an upper and lower bound for the positional parameters, and a resulting outcome in case the variable operational parameter exceeds or falls below the acceptable threshold. An example of such an upper bound is the maximum speed 340 shown in FIGS. 4A and 4B. The rules that produce the same operational parameters based on multiple variations in different positional parameters can be combined by Boolean logic operator to provide a multi-variable analysis of handpiece positional parameters.

Possible outcomes from controller 200 can include triggering an "operation" mode and a "stop" mode. In the "operation" mode, the treatment continues, as will be discussed in greater detail below, and the operational parameters of the apparatus 100 are monitored in real-time in response to the signals indicative of the changes in the handpiece positional parameters. In the "stop" mode, controller 200 immediately halts all operations of apparatus 100 in response to detecting a significant change in treatment conditions that render the continuation of treatment unsafe or ineffective. Specifically, treatment with the dosage level that exceeds the lower threshold, but is below the upper threshold is considered acceptable. Treatment at a dosage level that exceeds the upper threshold or is below the lower threshold level may require shutdown of apparatus 100.

A specific example of detector 170 usable in the apparatus 100 is an optical navigation sensor produced by Agilent Technologies, Inc. of Palo Alto, Calif., and particularly the ADNS 2600 series optical navigation engine. The optical navigation engine (i.e. image processing device 190) produces measurements of changes in the handpiece position by optically acquiring sequential surface images up to 2300 times per second and mathematically determining the direction and magnitude of the handpiece movement at the maximum of 400 counts per inch (cpi) and at speeds up to 12 inches per second (ips).

If an optical navigation sensor such as described in the previous paragraph is used for detector 170, then in some cases this detector can be made more robust by the addition of a substance to the target area 150, the substance having the effect of enhancing the contrast for the optical navigation sensor. Such a contrast enhancing substance may include, for example, particles, suspensions, colloids, emulsions or solutions. One example of particles that may be used as a contrast enhancing substance would be ink particles that are spread onto the skin by painting or marking the skin prior to treatment with the handpiece. Particles such as carbon particles or fluorescent particles may be used in some embodiments. As a further example, OptiGuide Blue dye produced by Reliant Technologies, Inc. of Palo Alto, Calif., may be used as the contrast enhancing substance. Contrast enhancing substances are not being used in this context solely or even primarily as absorbing targets or chromophores for a treatment or diagnostic wavelength, nor are they solely or primarily used as a means to show what areas have already been treated. Contrast enhancing substances may be effective due to their absorption or reflection of light. Skin is generally reflective for visible light wavelengths, so a contrast enhancing substance that is highly absorptive for the illuminating wavelength will be easily detectable. Alternately, using a contrast enhancing substance that is more reflective than skin for the illuminating wavelength will also improve the detectability.

The use of contrast enhancing substances, such as dyes, inks, particles, solutions, etc. that do not absorb the treatment wavelength, but which enhance the contrast of the viewing of the treatment surface by the detection system, allows the detection to have high signal-to-noise ratio (SNR) and subsequently good surface quality (SQUAL) values, which in turn improves the safety and reliability of the treatment. Different dyes have different visual effects. For example, a dye including cyan blue (FD&C Blue #1) may look rather unnatural to patients and sometimes may cause post treatment staining of certain skin types, resulting in more post treatment cleaning than may be desirable. It should be noted that darker skin types have higher SQUAL values than lighter skin types using a red LED (610 nm-650 nm), due to the presence of easily detected patterns of melanin in darker skin.

The contrast enhancing substance may be chosen based in part on skin tone and the wavelength of light used by the detection system. Thus, a red LED in the detection system may be enhanced in its detection sensitivity by applying blue or black dye, ink or particles to the tissue surface. A blue LED used with yellow dye, ink or particle provides enhanced contrast. For example, an Orange-Red LED combined with a silicon mouse detection chip works well with a blue dye. The blue dye may have some issues as described above. However, by adding subtractive red and yellow dyes to a bright blue dye, the result is a brown dye that is less distracting to view, and, when removed after treatment, does not need to be removed completely for the patient to appear to have a relatively normal skin tone. In fact, proper design of the dye allows either no residue, similar residue ratio of the original dye mixture, red residue that blends in with the erythema post-treatment, or even a slight green residue to help cover the erythema caused by the treatment and to act as a cosmetic post-treatment cover up. The addition of the reds and yellows does not impair the performance of the robotic sensor, since the contrast is determined primarily by the blue dye concentration and by the variations of the dye thickness as it accumulates in dermatoglyphic folds in the skin or is purposely applied with an applicator that creates a speckled pattern for the detector to identify for purposes of focus detection and velocity or position detection. The use of red and yellow for the LED also adds no subtractive colorant to the robotic view. In other words, viewed in the light of the LED, the appearance of the skin is the same as whether with the pure blue dye or with the brown dye. The broad spectral sensitivity of the human eye sees the image quiet differently, blue versus brown. Dyes such as the following examples have been used: FD&C Blue #1, FD&C Red #40, FD&C Yellow #5, FD&C Yellow #6, D&C Red #22, and D&C Red #33.

The dye may also be used as a targeting mechanism as well. For example, in treating telangiectasias or spider veins on the legs, a Q-tip or similar applicator may be used to dye the target by staining the target and/or the overlying stratum corneum. Since the dye can be applied carefully and adjusted if necessary to match the target, treatment is then quick and accurate. In addition, the longer treatment path along the length of the blood vessel helps to heat the moving blood and eliminate the cooling effect thereof. Treatment in a direction orthogonal to the blood vessel may also be used. Pressure applied to the contact tip may further assist in treating vascular lesions or vessels. In the case of darker skin, two dyes—one dye to trigger the robot system and another dye to turn it off by purposely reducing the SQUAL value—may provide more effective treatment. Multiple dyes may be used for any skin type or color, depending on the intended result and the treatment and/or detection system being used.

A further example of a contrast enhancing substance is a fluorescing dye that absorbs at the imaging wavelength(s) but is transmissive to the treatment wavelength(s). Steady state fluorescence without bleaching may improve the SNR of the imaging system, especially in the near infrared (NIR) spectrum since photo-sensor arrays are most sensitive in that region. The addition of fluorescence reduces the need for a high power illumination source. However, this may involve optical system design that incorporates imaging at both the illumination and fluorescence wavelengths to minimize chromatic aberrations. The dye should be non-toxic and should not bleach at typical treatment temperatures (i.e. temperatures less than about 110° C.).

In embodiments using contrast enhancing substances such as dyes, inks solutions or suspensions, application of the contrast enhancing substance may be achieved simply by applying the substance onto the skin with a cotton swab or other applicator. The substance should typically be evenly spread out and left to dry, although being evenly spread out or allowed to dry are not required in all cases. This process uses the natural skin irregularities and folds where the substance infiltrates or accumulates to enhance the contrast for imaging. Typically, a thicker layer of substance remains within skin folds, while in general less substance stays on flatter potions of the skin. The substance stains may appear random, patchy, and irregular, enhancing the natural features and the observed contrast of the skin to be imaged. Relative position and velocity values can be extracted based on this simple process. The technique does not require placement of regular patterns or graphics on the skin to be useful. Detecting relative position or velocity of a hand-piece or an element from which treatment radiation is emitted in relation to the tissue being treated may then be used to control one or more aspects of the system. The hand-piece or element emitting radiation may be in contact with the tissue or not in contact with the tissue. The optical system and/or scanning system may be altered to change such parameters as focal depth, beam direction, beam shape or size, scanning speed, scanning direction for multi-dimensional scanning systems. More specifically, de-blurring of the treatment zones can be achieved by altering one or more of these parameters in response to changes in velocity of a hand-piece. For example, the scanning speed and/or beam shape and direction may be altered to compensate for the movement of a handpiece relative to the tissue, and preferably such parameters may be altered in response to changes in velocity of the handpiece. For example, as the handpiece is moved more quickly over the tissue, the scanning speed of a scanning element in the system may be increased to match the movement. Alternately, the optical system may be altered to hold a treatment beam on a given treatment zone for a desired time while the handpiece moves. Scanning systems may include galvanometers, piezoelectric elements, mechanical scanning elements, MEMs, nanotechnology, rotating mirrors or optical elements, holographic elements, diffractive elements, acousto-optic elements, etc.

Alternatively, a capacitive sensor array, such as a precision silicon sensor 5thSense-USB series manufactured by Veridicom, Inc. of Sunnyvale, Calif., may be used to detect variations in the handpiece positional parameters. In the capacitive sensor array, the surface of the sensor consists of a silicon chip containing an array of 90,000 capacitor plates with sensing circuitry at 500-dpi pitch. The capacitor sensing plates create an 8-bit image of the ridges and valleys of the target tissue area pressed against the chip. This information is converted to a video signal to create a video image that is subsequently analyzed and converted to binary form to become a unique image template. Changes in the template correspond to changes in the position of the handpiece 140 relative to the target area 150. The high-speed optical navigation detectors are easier to package into a handpiece and would be preferable for the measurements of the handpiece positional parameters.

Another example of a detector 170 that could be used in apparatus 100 is an accelerometer, for example to measure in real-time the velocity of the handpiece relative to the tissue to be treated. An example of such an accelerometer is the ADXL202/ADXL210 iMEMS® Accelerometers manufactured by Analog Devices, of Norwood, Mass. Typically, a signal from an accelerometer provides an indication of the acceleration of the device. Such acceleration signals may then be processed, for example by a processor or DSP using an integration function, to provide the velocity of the device. Alternate embodiments of the present invention may include profilometer-type detectors for determining relative location or movement of the device. Further, alternate embodiments performing similar functions (i.e. determining movement, location, velocity, acceleration, etc.) may include MEMS, micro-mechanical-optical devices, or nanotechnology devices to determine relative location, velocity and/or acceleration.

As mentioned earlier, it is preferred to control the operational parameters of apparatus 100 so that the dosage of treatment is maintained uniformly across the target area 150 during the entire treatment. Advantageously, apparatus 100 is adapted to characterize variations in the handpiece positional parameters as the source of change in the treatment dosage and use the outcomes of application of algorithms executed by controller 200 to control in real-time operational parameters of apparatus 100 for improved uniformity, safety, and efficiency of the treatment.

From the graphs shown in FIGS. 4B and 5B, it is evident that by monitoring the operational parameters of apparatus 100 in response to the changes in the handpiece positional parameters, the dosage of the treatment can be maintained in real-time at the desirable pre-selected level throughout the treatment period across the entire target area 150. Specifically,.as described below, by using apparatus 100, adjustment to any one or more of the handpiece operational parameters (e.g., optical operational parameters and delivery system parameters) may be performed in response to a variation in any one or more positional parameters. Apparatus 100 can in real-time compensate for the imprecision of movement of the human hand, whereby the tissue treatment can be delivered to the target tissue at the pre-selected level with greater uniformity, safety and efficiency.

Returning to FIG. 1, apparatus 100 advantageously includes controller 200 for adjusting in real-time the range of operational parameters of the light beam in response to detected variations in the handpiece positional parameters.

Controller 200 may be a general purpose programmable digital computer connected to detector 170 to receive a precise digital output. Controller 200 can be programmed to sample in real-time variations in the handpiece positional parameters; to display the positional parameters measurements on the display monitor (not shown); to store the measurements; to apply the treatment criteria logic to the measured signals for determining necessary adjustments in operational parameters, and to implement adjustments to at least one operational parameter while the treatment continues. Possible criteria for the treatment logic may include changes in the position or the velocity of the handpiece relative to the target area 150, changes in angle of the handpiece relative to the target area 150, changes in the distance of the handpiece from the target area 150, or combinations thereof.

Controller 200 may comprise interface unit 210 for receiving and processing signals indicative of the variations in the positional parameters from detector 170, analyzing the signals, sending signals requesting determination of suitable operational parameters; and performing adjustments to the signals indicative of operational parameters. Interface unit 210 may include analog processing circuitry (not shown) for normalization or amplification of the signals from detector 170 and an analog to digital converter (not shown) for conversion analog signals to digital signals. Interface unit 210 may be operably coupled to the components of apparatus 100, i.e., power source 110, light emitter 120, and actuator 145 for selecting initial operational parameters for the tissue treatment and for controllably adjusting in real-time components of the apparatus 100 to generate new suitable operational parameters.

Controller 200 may further include processor 202 for determining a set of desired operational parameters in response to the signals from interface unit 210 indicative of the changes in the treatment dosage. Processor 202 may be embodied as a microprocessor, an ASIC, DSP, controller or other processing means that are suitable for determining the desired operational parameters. Upon receiving the signals from interface 210, processor 202 determines a new set of suitable operational parameters. Examples of operational parameters for the light emitter 120 are optical power, pulse repetition rate, pulse energy, pulse duty cycle, and wavelength. Examples of other operational parameters are handpiece temperature, handpiece vibration intensity, handpiece vacuum suction activation, actuator 145 movement rate, and actuator 145 movement pattern. Processor 202 may include computational means (not shown) for calculating specific operational parameters, or may be based on neural networks and fuzzy logic techniques for systematically arriving at optimal operational parameters for the desired treatment using the software of this invention. Alternatively, the computational means may comprise one or more memory look-up tables for generating operational parameters values for the pre-selected treatment given the measured positional parameters or the treatment dosage. Memory look-up tables would provide coherent data sets of signal values from detector 170 and corresponding values of desirable operational parameters. Thus, the software of the invention associated with controller 200 allows processor 202 to perform in real-time mapping of operational parameters of apparatus 100 as a function of the handpiece positional parameters and output the set of the desired operational parameters to interface unit 210.

The new operational parameters determined by controller 200 are communicated to the components of apparatus 100 through the interface unit 210. Specifically, interface unit 210 may be coupled to the power source 110. Interface unit 210 can command in real-time the power source 110 to increase or decrease power output of light emitter 120 based on the information received from detector 170. Thus, the power provided by light emitter 120 can be adjusted in real-time in response to the changes in the handpiece positional parameters to generate new treatment operational parameters and effect a new treatment rate that corresponds to the pre-selected treatment dosage.

In operation, initial operational parameters are defined for a desired pre-selected tissue treatment, and the data is entered via interface unit 210 to set operational modes of the components of apparatus 100. Accordingly, energy generated by power source 110 and properties of the light beam emitted from emitter 120 are characterized by the initial operational parameters. The light beam is transmitted through optical fiber 130 to handpiece 140 and then focused by optical element 160 that is set in the initial operating position for delivering the pre-selected tissue treatment to target area 150. Handpiece 140 is moved by a physician's hand along target area 150.

When the positional parameters of handpiece 140 change during the course of treatment, detector 170 detects the change in the treatment dosage resulting from the variation in one or more positional parameters. Using software, firmware or even solid-state elements in embodiments of the present invention, detector 170 determines whether the variation of the delivered dosage is above or below the pre-selected treatment dosage threshold.

Detector 170 determines variations in a repeatable and accurate manner by employing sensor 180 and image-processing device 190. Sensor 180 tracks and analyzes in real-time the two-dimensional or three-dimensional movements of the handpiece 140 relative to the target area 150. Images of the target tissue produced by sensor 180 are recorded and processed by image processing device 190 to yield an indication of deviation in the treatment dosage resulting from variations in the handpiece positional parameters.

If the deviation is above the upper threshold or below the lower threshold, a "stop" signal may be sent from controller 200 to halt operation of the apparatus 100, thus preventing patient's exposure to unsafe treatment. When the deviation is within the pre-selected acceptable treatment dosage range, a signal indicative of the value of actual variation from the pre-selected treatment dosage treatment may be continued.

Interface unit 210 of controller 200 stores measurements received from detector 170 and invokes processor 202 to calculate in real-time a set of new operational parameters corresponding to the varied positional parameters. Using the software of this invention, processor 202 calculates the new operational parameters in real time by essentially continuously updating operational parameters as a function of the positional parameters. The signals indicative of the new set of the desired operational parameters are transmitted back to interface unit 210.

Interface unit 210 essentially continuously monitors and takes measurements of actual operational parameters of apparatus 100. During treatment, interface unit 210 compares in real-time the measured values of actual operational parameters with the calculated set of operational parameters received from processor 202. When the measured values of one or more operational parameters vary from the calculated values, interface unit 210 applies the information to control the power source 110, emitter 120 and optical element 160 in accordance with the pre-selected tissue treatment. More specifically, interface unit 210 sends signals to the components of apparatus 100 that modify in real-time the operational modes of the components. The components are then enabled for generating operational parameters for the laser treatment at the desired new values. The new values of operational parameters effectuate a new rate and/or configuration of laser treatment that corresponds to the pre-selected treatment dosage at the varied handpiece positional parameters. This tends to subject target area 150 to the treatment level that closely approximate the pre-selected level because the delivered dosage (i.e., radiant exposure in joules/cm$^2$) and the density of microscopic pattern are maintained unchanged.

For example, the wavelength or the power of treating light beam emitted by light emitter 120 may be adjusted according to the measured values. A plurality of ranges of the light beam wavelengths may be stored in the memory of the processor 202 to select from. Alternatively, a new wavelength can be calculated in response to a signal from detector 170 indicative of variation in the treatment dosage resulting from variations in the handpiece positional parameters. Measured in real-time actual value of the light beam wavelength may be compared during treatment by interface 210 to a corresponding stored or calculated value of wavelength provided by processor 202. The wavelength of the treating light may be then reset by adjusting in real-time the continuous output or the cycle of light emitter120 according to the relations between measured values and stored/calculated ranges. The tissue treatment continues with the new wavelength appropriate for the new position or velocity of the handpiece at the pre-selected treatment dosage.

Figure 8:
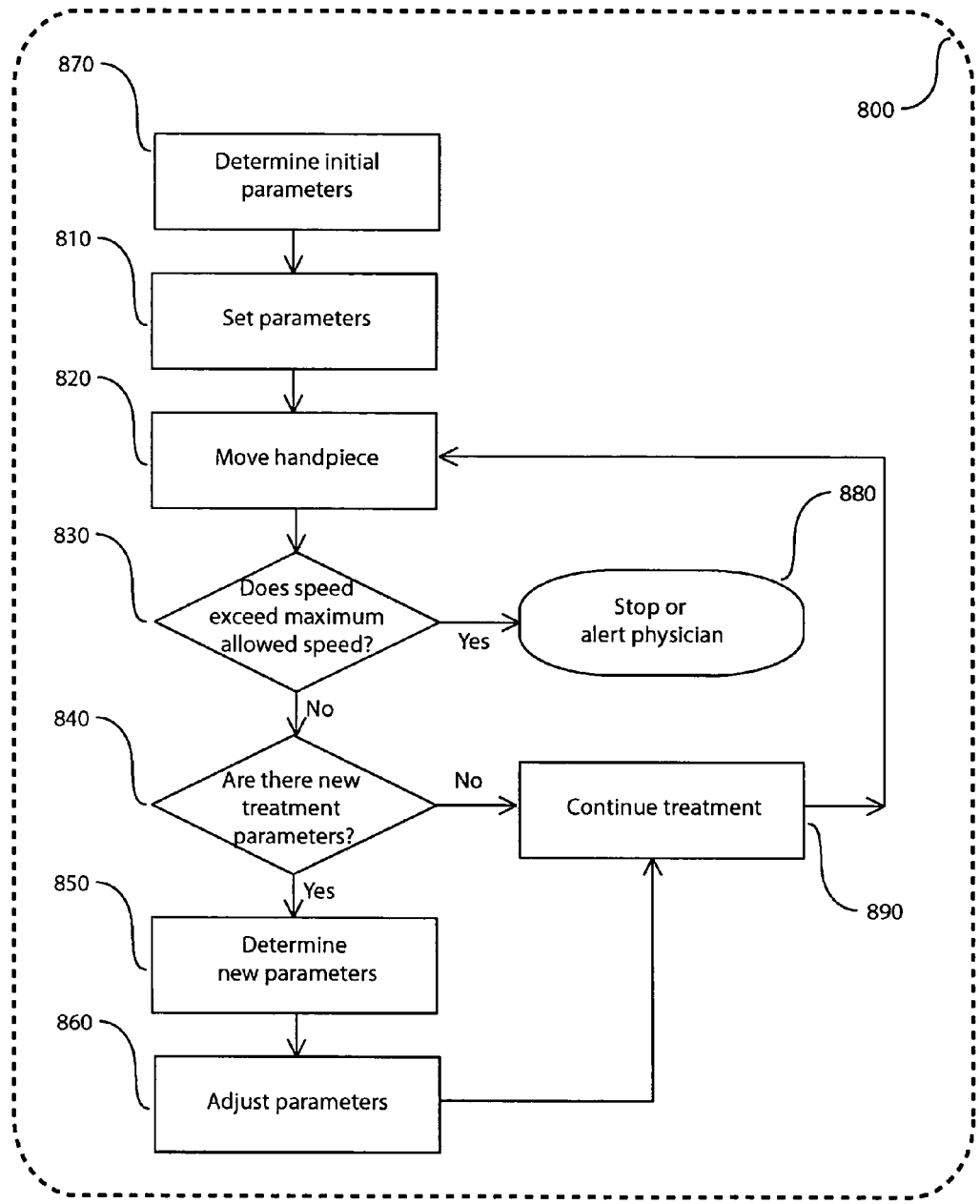
FIG. 8 is an example of a flow chart of a method of determining and adjusting in real-time operational parameters of a handpiece based on variation in at least one positional parameter (handpiece speed) during pre-selected tissue treatment.

An example of a laser-induced tissue treatment process 800 in accordance with the present invention is exhibited in FIG. 8. Process 800 generally includes a parameter setting step 810, moving step 820, measuring step 830, evaluation step 840, determining step 850, adjusting step 860, and continuing step 890. Process 800 may also suitably include an initial pre-selecting step 870 and an alert step 880.

Parameter setting step 810 generally includes entering optical operational parameters in the memory of the interface unit 210 and emitting a plurality of light beams with the selected operational parameters from emitter 120, via optical fibers 130 and handpiece 140, towards the patient's tissue to be treated (i.e. target area 150). The treatment operational parameters may include the laser power, light beam intensity, wavelength, rate of emission, pulsation rate, pulse duration treatment, temperature, etc. Entered operational parameters are preferably selected such that a particular pre-selected dermatological treatment for a particular patient would be delivered from the application of the light beam to target area 150.

During moving step 820, the handpiece 140 is moved by a physician's hand along target area 150. The movement of handpiece 140 is defined by positional parameters, e.g., the velocity, the distance from the target area, and the position relative to the target area 150. It is preferred for the reasons of uniformity, safety and efficiency of treatment, that certain positional parameters of handpiece 140 be maintained at a constant level, e.g., the treatment is preferably delivered at a constant speed, preferably at approximately 10 mm/s, and with precision in the distance and positioning of handpiece 140 relative to the target area. Specifically, output 148 of handpiece 140 should be continuously located at a constant distance from the surface of target tissue area 150, and the handpiece should be positioned to enable propagation of the light beam from outlet 148 approximately at a right angle. When the handpiece positional parameters vary during moving step 820 due to the imprecision of manual operation, the variations result in changes in the treatment dosage and the microscopic pattern of the discrete treatment zones.

In measuring step 830, a variation in at least one positional parameter is detected and measured in real-time while the treatment continues. Once the variation occurs, it is detected and recorded by detector 170. Detector 170 determines variations in positional parameters in a repeatable and accurate manner using sensor 180 and image processing device 190. Sensor 180 analyzes in real-time the motion of the handpiece 140 and produces a plurality of images that are recorded and processed by image processing device 190. Image processing device 190 determines variations in the handpiece positional parameters in a real-time mapping procedure, from which variations in the handpiece operational parameters are calculated by controller 200. Specifically, in measuring step 830, the detector 170 may be used to measure the movement of the handpiece to ensure that it does not exceed the upper bound of each positional parameter, for example, the maximum handpiece allowed speed. If the maximum allowed speed is exceeded, the controller 200 may stop the operation of apparatus 100 to avoid improper treatment. Alternatively, a visual or sound alarm may be initiated by the controller 200 to alert the physician to the improper procedure (Step 880). During step 830, handpiece 140 may be suitably moved by a physician's hand, allowing for measurements around repeated circular paths along target area 150. In accordance with an exemplary embodiment of the present invention, any number of measurements may be taken over any amount of surface of target area 150.

During analyzing step 840, controller 200 further analyzes the magnitude of the detected variations in the handpiece positional parameters to determine if adjustments to the treatment operational parameters are warranted. If the analyzed variations in positional parameters are minor, no adjustments to the operational parameters are necessary because the effect of such variation on the treatment dosage is insignificant. The treatment process will then continue at the pre-selected dosage (Step 890).

If the variation in at least one positional parameter is above the lower bound established by the algorithm rules, new operational parameters of the light beam, including possibly the rate of emission, power level, light beam intensity, pulsation rate, treatment temperature, etc., are determined in determining step 850.

Specifically, in determining step 850, a computational means of processor 202 uses an algorithm to calculate in real-time specific operational parameters corresponding to the changed positional parameters of handpiece 140 based on the signals from detector 170. The operational parameters are calculated such that the implementation of the new operational parameters would allow the pre-selected tissue treatment to continue unchanged or at a desired dosage that can be calculated based on the positional parameters of handpiece 140. The determining step 850 may include acquiring, processing, normalizing and converting by interface unit 210 signals generated by detector 170.

In another implementation, determining step 850 may be based on using proprietary memory look-up tables for generating operational parameters values given the measured variations in positional parameters or the treatment dosage. Memory look-up tables would provide coherent data sets of signal values from detector 170 and corresponding values of desirable operational parameters. Alternatively, the determining step 850 may be based on using neural networks and fuzzy logic techniques for systematically arriving at optimal operational parameters for the desired pre-selected treatment.

In adjusting step 860, interface unit 210 receives new operational parameters from processor 202 and applies proprietary software of this invention to adjust in real-time operating modes of at least one of the components of apparatus 100, including power source 110, light emitter 120, and actuator 145, to affect new operational parameters. Operating the components of apparatus 100 with new operational parameters at varied positional parameters allows for delivery of the tissue treatment at a new rate, such that the level of the treatment closely approximates the pre-selected level, i.e., the dosage (i.e., radiant exposure in $J/cm^2$) and density of microscopic pattern are maintained unchanged or are changed in a desirable manner. One or more pre-selected treatment programs may be selected for subsequent treatment to achieve new operational parameters. Any one or more components of apparatus 100 may be adjusted in adjusting step.860. Step 860 may be repeated as desired until the pre-selected treatment dosage is obtained.

In continuing step 890, the treatment of target area 150 continues with new operational parameters that are automatically controlled and continuously adjusted, whereby the tissue treatment remains at the desired dosage level.

In addition to the steps noted above, process 800 may include an initial calculating step 870. In the initial calculating step 870, initial operational parameters are calculated for a particular patient. In other words, the operational parameters selected in step 810 may be based on the initial calculating step whereby the operational parameters are calculated as a function of the individual tissue properties and the desired results of the treatment pre-selected for a particular patient.

FURTHER EXAMPLE EMBODIMENTS

Various further embodiments of the present invention showing examples of systems and methods for compensating de-blurring effects will now be described. As noted above, being able to move the handpiece at varying speeds without altering the treatment dosage and/or treatment pattern is a significant benefit of the present invention. If no feedback control based on handpiece movement is included in a laser treatment system that includes a handpiece moved by human hand, then typically dosage and/or treatment pattern will be impacted. Typically, this may include spreading out the treatment pattern and blurring the individual discrete treatment zones by elongating the zones along the direction of handpiece movement.

Two approaches to counteracting the blurring effects of handpiece movement include angular beam deviation and translational beam motion. FIGS. 9 and 10a-c show illustrations of these approaches. Some embodiments may include both of these approaches.

Figure 9:
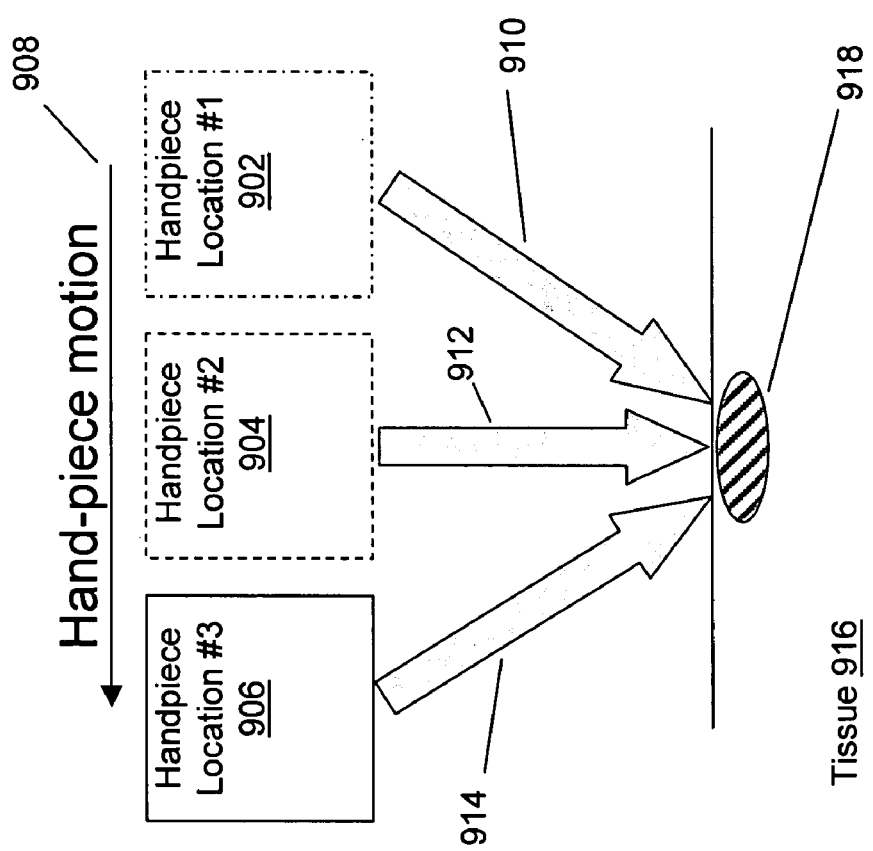
FIG. 9 shows an embodiment utilizing angular beam deviation.

FIG. 9 illustrates in diagrammatic form a handpiece (902, 904, 906) being moved 908 relative to tissue 916. A treatment zone 918 is being treated by the treatment beam 910, 912, 914 as the handpiece is moved. The handpiece and the treatment beam are shown in three representative locations during the handpiece movement from Handpiece location #1 902 to Handpiece Location #3 906 with the treatment beam consequently changing from treatment beam configuration 910 to treatment beam configuration 914. Thus, the treatment beam remains directed at treatment zone 918 throughout the movement of the handpiece from Handpiece location #1 902 to Handpiece Location #3 906. The treatment beam may be continuous wave (CW) or pulsed during the movement from Handpiece location #1 902 to Handpiece Location #3 906. As described in further detail below, the optical system and/or delivery system is controlled to produce the angular beam deviation. It will be understood that the handpiece may be held stationary and the tissue 916 may be moved relative to the handpiece.

Figures 10A, 10B, 10C:
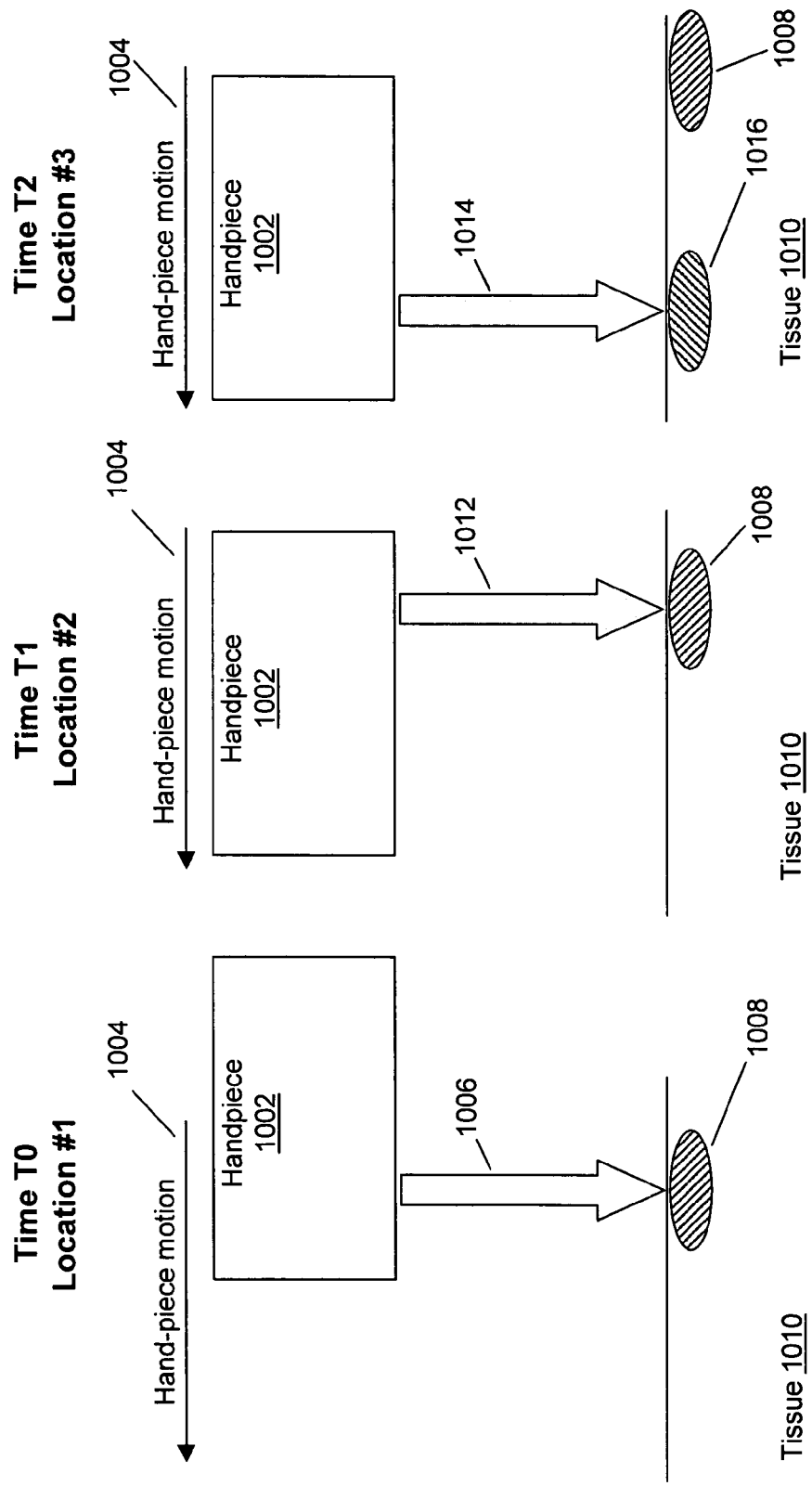
FIGS. 10a, 10b and 10c show an embodiment using direct translational beam motion.

FIGS. 10a-10c illustrates in diagrammatic form a handpiece 1002 being moved 1004 relative to tissue 1010. A treatment zone 1008 is being treated by the treatment beam 1006, 1012, 1014 as the handpiece is moved. The handpiece and the treatment beam are shown in three representative locations during the handpiece movement from Time T0/Location #1 to Time T1/Location #2 with the treatment beam consequently changing from treatment beam configuration 1006 to treatment beam configuration 1012. Thus, the treatment beam remains directed at treatment zone 1008 throughout the movement of the handpiece from Time T0/Location #1 to Time T1/Location #2. The treatment beam may be continuous wave (CW) or pulsed during the movement from Time T0/Location #1 to Time T1/Location #2. As described in further detail below, the optical system and/or delivery system is controlled to produce this translational beam motion. Unlike angular beam deviation as illustrated in FIG. 9, the angle of the treatment beam in a translational beam deviation approach remains substantially unchanged during the motion of the handpiece. In translational beam motion, typically the beam exit location from the handpiece 1002 changes in a direction to counteract the motion of the handpiece. Thus, the treatment beam stays over the first treatment zone 1008 from Time T0/Location #1 to Time T1/Location #2. When the treatment of the first treatment zone 1008 is completed, a second treatment zone 1016 may then be treated by treatment beam 1014 as the handpiece is at Time T2/Location #3. It will be understood that the handpiece may be held stationary and the tissue 1010 may be moved relative to the handpiece.

Figure 11A:
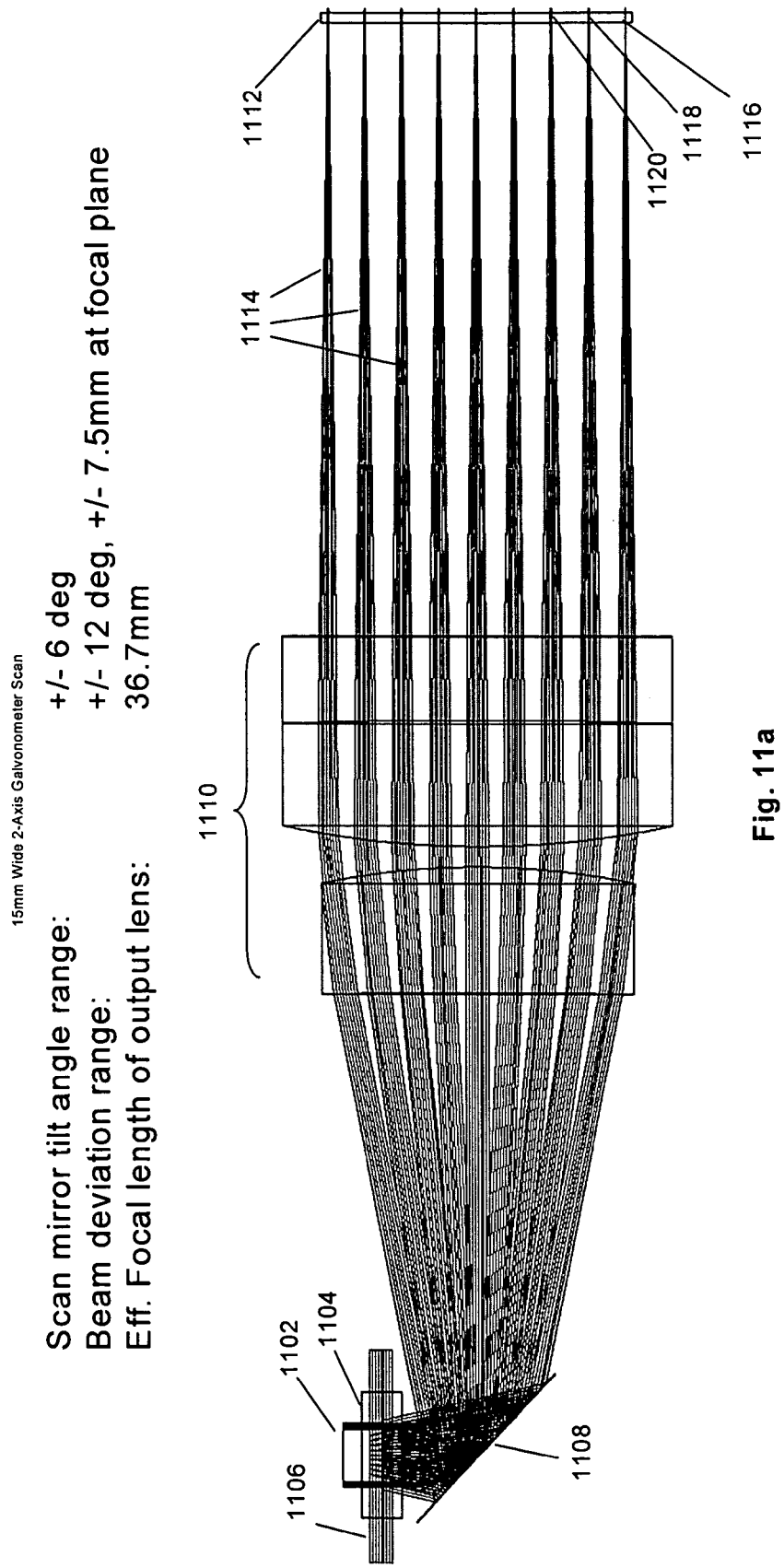

FIG. 11a illustrates an embodiment of the present invention utilizing a two-axis galvanometer scan system as an example of an angular beam deviation approach. A light beam 1106, and typically a laser beam, is directed to a crossed set of mirrors 1102, 1104 having galvanometer actuators to tilt them. The light beam exiting the crossed set of mirrors 1102, 1104 is then redirected by a mirror 1108 and passed through an imaging lens set 1110 and directed to tissue 1112. One skilled in the art will recognize that mirror 1108 is not necessary to the operation of this system, and further imaging lens set 1110 may take a variety of configurations. Scan mirror 1102 tilts around an axis such that the light beam is deflected through the system to discrete treatment zones, such as, for example, 1116, 1118, 1120. The galvanometer coupled to scan mirror 1102 (not explicitly shown in FIG. 11a) operates to rotate the scan mirror 1102 so as to control the location of the treatment beam(s) 1114 at the tissue 1112. A handpiece (not shown) through which the treatment beam(s) 1114 pass in treating the tissue 1112 may be moved in a direction perpendicular to the plane of the paper in FIG. 11a. To counteract the effects of such movement, a de-blurring mirror 1104 is titled by a galvanometer (not explicitly shown in FIG. 11a) coupled thereto such that the individual treatment beam(s) 1114 remain on their respective discrete treatment zones (e.g., 1116, 1118, 1120) for the desired treatment time and dosage. For example, if the handpiece is moved out of the plane of the page of FIG. 11a towards the viewer, then de-blurring mirror 1104 would tilt so as to cause the treatment beam(s) 1114 to stay on the respective treatment zone(s) by changing the angle of the treatment beam(s) such that they move into the plane of the page away from the viewer relative to the handpiece movement. From the perspective of the tissue 1112, the treatment beam(s) would simply appear to stay on the respective discrete treatment zone(s) while the handpiece moved, and then, at the completion of the treatment dose for the first set of discrete treatment zones, the treatment beam(s) 1114 would appear to jump to the next set of discrete treatment zones.

Various dimensions and system parameters are shown in FIG. 11a as examples. One skilled in the art will recognize that these example parameters and dimensions may be varied depending on the desired output and system configuration without altering the basic concepts of the methods and apparatus illustrated here. Further, single beam systems may be similarly configured, wherein the scanning mirror 1102 of FIG. 11a may not be required. Further, other tilting or rotating mechanisms may be used in conjunction with the scanning and/or blurring mirrors, such as, for example, piezoelectrics, motors, mechanical systems, MEMS, and so forth. The mirrors may also be replaced by diffractive elements and holographic elements. The scanning mechanisms may alternately be acousto-optical or electro-optical.

FIG. 11b illustrates an example of results for the embodiment described above with reference to FIG. 11a. FIG. 11b shows two sets of discrete treatment zones (1154, 1156) illustrating de-blurring for different speed handpiece movements. For a relatively higher speed handpiece motion 1130, nine discrete treatment zones (e.g., 1134 and 1136) are shown in a line perpendicular to the direction of handpiece motion (see 1154). Each set of three spots depicts a single treatment zone relative to the handpiece. For example, for single treatment zone 1134, spots 1142, 1144 and 1146 overlap to form the single discrete treatment zone 1134. As the handpiece moves in the direction of motion 1130, the treatment beam starts at spot 1142 and travels in a direction opposite to the handpiece motion from spot 1142 to spot 1146. Due to the handpiece movement, spots 1142, 1144 and 1146 overlap as they are controlled in spacing and timing to counteract the handpiece motion. From the perspective of the tissue, the spots overlap substantially exactly, such that a single discrete treatment zone is created. In this example, a 1200 micron deblur is used to counteract the relative higher speed. For a relatively lower speed handpiece motion 1132, a 500 micron deblur 1156 may be enough to counteract the handpiece motion. A single discrete treatment zone 1138 in this example has more closely spaced spots 1148, 1150, 1152. One skilled in the art will understand that other deblur dimensions besides the 500-micron and 1200-micron examples discussed above are included in the present invention and depend on the speed of handpiece movement. In either case, a continuous treatment beam may be used as the de-blurring is accomplished for a given discrete treatment zone or set of such zones. Alternately, a pulsed beam may be used, in which case three separate pulses may be used to correspond literally to the three spots shown in FIG. 11b for the discrete treatment zones.

Figure 12:
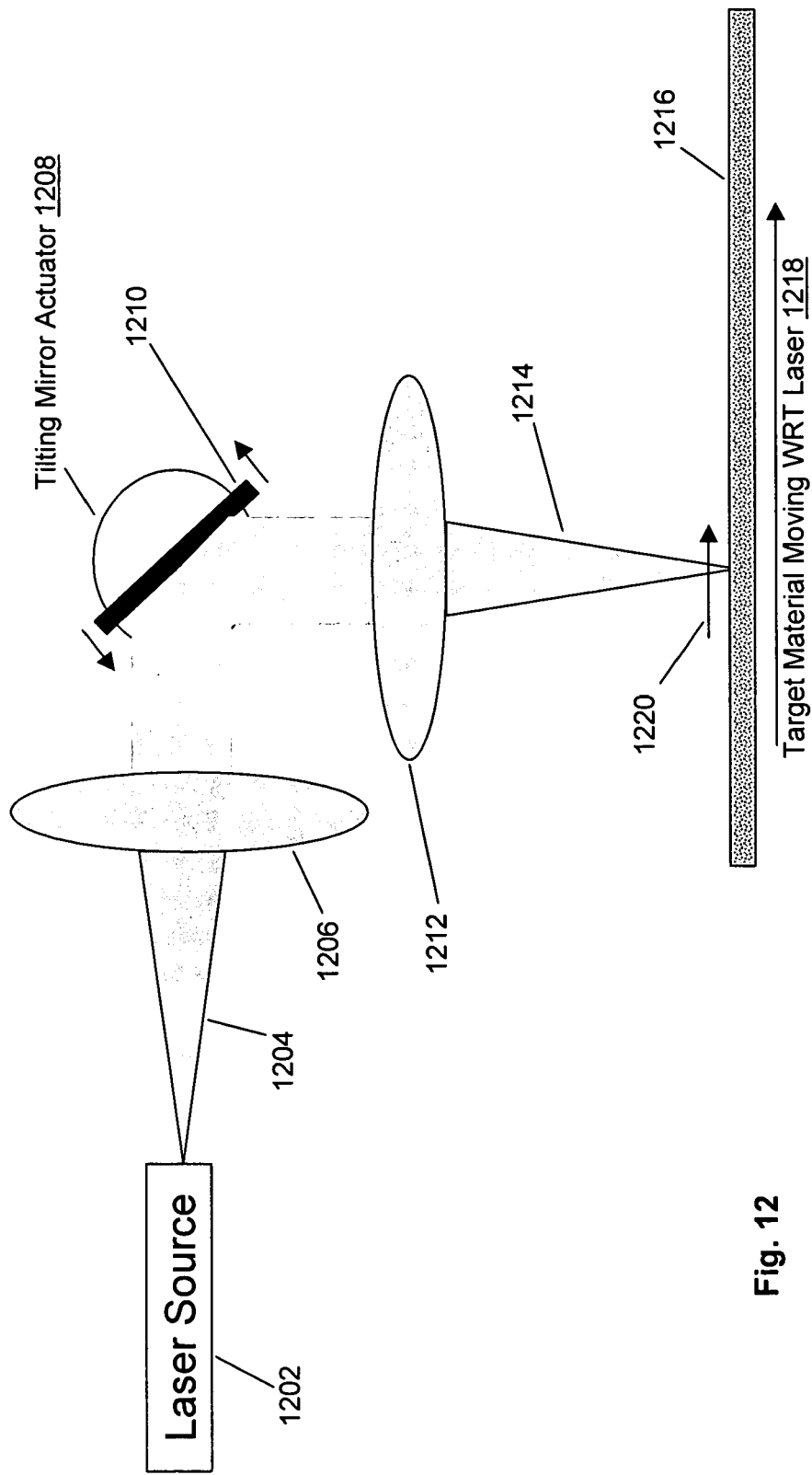
FIG. 12 is an example of an embodiment of the present invention having a tilting mirror actuator.

FIG. 12 shows an example of a further embodiment of the present invention utilizing angular beam deviation. In this example, a laser source 1202 emits light 1204 that is passed through optical element 1206 and then is re-directed by mirror 1210 coupled to tilting mirror actuator 1208. The redirected light then passes through one or more optical elements 1212 to form the treatment beam 1214 that is used to treat tissue 1216. The treatment beam typically is emitted from a handpiece (not shown). As the tissue moves 1218 relative to the laser and/or handpiece, the treatment beam 1214 moves 1220 substantially in synchronization with the movement. Thus, the treatment beam 1214 remains substantially on a single treatment zone for the duration of the desired treatment and dosage, regardless of the handpiece motion during that duration. This de-blurring compensation is accomplished by titling the mirror 1210 to alter the direction of the treatment beam 1214. Such titling of mirror 1210 may alter the angle that the treatment beam exits the handpiece and/or optical element 1212, and/or the mirror tilt may alter the exit location of the treatment beam from the handpiece. Tilting actuator 1208 may include a galvanometer, a piezo-electric element, MEMS technology, a motor, and so forth.

A further embodiment of the present invention includes counter-rotating wheels with optical elements on the rotating wheels. The optical elements may include transmissive (e.g., lenses, wedges), reflective, diffractive or holographic elements. Examples of such embodiments are described in co-pending patent application, U.S. patent application Ser. No. 10/750,790, filed on Dec. 31, 2003, and entitled "High Speed, High Efficiency Optical Pattern Generator Using Rotational Optical Elements," which is incorporated by reference herein in its entirety. By altering the tilt and/or rotational configuration of the optical elements on the counter-rotating wheels, de-blurring may be achieved.

Figure 13:
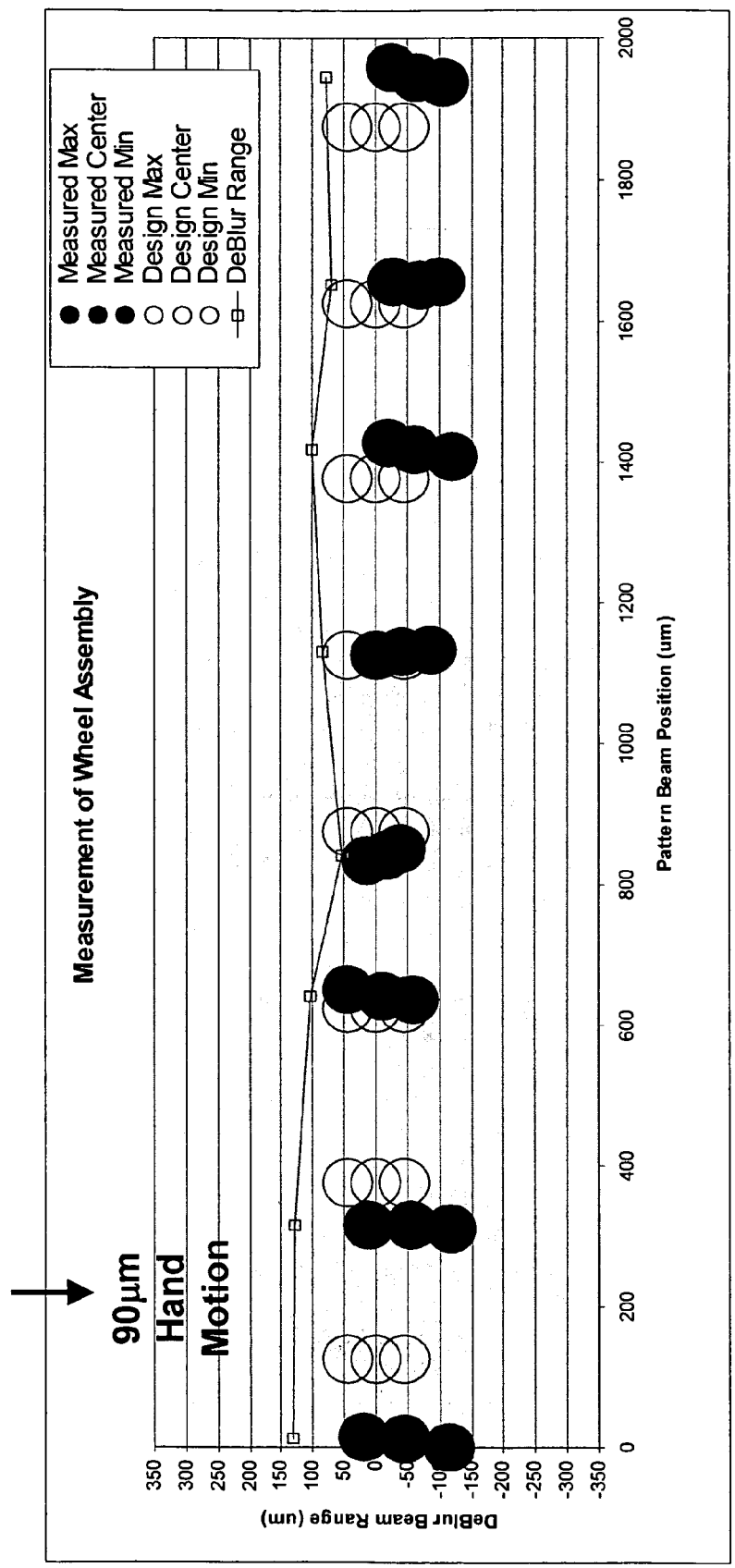
FIG. 13 shows a simulation of treatment zones for an embodiment of the present invention utilizing counter-rotating optical elements.

FIG. 13 shows example results for a counter-rotating lens embodiment. FIG. 13 shows measured and expected results for one line of eight discrete treatment zones. The beam position spots for each such discrete treatment zone are shown with reference to the handpiece which is moving in the indicated direction. Each set of three dark overlapping beam position spots shown in FIG. 13 correspond to a single discrete treatment zone. The beam position spots are created in a sequence that is opposite to the direction of handpiece motion.

FIGS. 14a and 14b illustrate examples of further embodiments of the present invention in which translational beam motion is utilized. FIG. 14a shows an example of an optical fiber array 1402 including a number of optical fibers (e.g., 1404 and 1406). One or more beams of radiation may be transmitted through the optical fibers simultaneously or sequentially. FIG. 14b is a side view of fiber array 1402. The distal end of fiber array 1402 (i.e. the end closest to tissue to be treated) may be coupled to and/or incorporated within a handpiece (not shown). In the example shown in FIG. 14b, a piezo-electric (PZT) 1412 element is in contact with and/or coupled to one or more optical fibers 1404. PZT 1412 is also in contact with and/or coupled to an anchor portion 1414 of fiber array 1402 and/or the handpiece. PZT 1412 operates to shift optical fiber 1404 in a direction typically opposite to the direction of handpiece motion 1408. Thus, during movement of the handpiece and/or fiber array 1402, optical fiber 1404 is held over a discrete treatment zone of tissue (not shown) to counteract blurring and to provide desired treatment and dosage. PZT 1412 may operate to move the optical fiber 1404 and/or to change the angle of the optical fiber 1404 relative to the tissue. The optical fiber 1404 is typically flexible such that it can be moved and/or bent relative to the fiber array and/or handpiece. One or more PZTs may be included and coupled to one or more optical fibers, such that separate optical fibers may be moved separately.

Although the present invention is set forth herein in the context of the appended drawing figures, it should be appreciated that the invention is not limited to the specific form shown. For example, while the inventive method and apparatus are conveniently described as configured to treat human tissue in microscopic patterns, the process of adjusting in real-time operational parameters based on variations in positional parameters of a system treating macroscopic domains, open patterns, spatial targeting of lesions, etc., are considered within the scope of this invention. In addition, the invention is not limited to dermatology and could be advantageously used in other technologies using light or laser treatment. Various other modifications, variations, and enhancements in the design and arrangement of laser-induced tissue treatment methods and apparatus as set forth herein may be made without departing from the spirit and scope of the present invention as set forth in the appended claims.

The invention claimed is:

1. An apparatus for controlled tissue treatment comprising:
   a light emitter that emits at least one light beam;
   a moveable handpiece adapted to deliver the at least one light beam to an area of tissue to be treated in a pattern of discrete treatment zones during movement of the handpiece across the area of tissue, wherein a tissue treatment depends upon one or more operational parameters of the at least one light beam, and the movement of the hand piece across the area of tissue is defined by a plurality of variable positional parameters such that variation in at least one positional parameter affects the tissue treatment;
   a controller operably coupled to the handpiece for controlling the one or more operational parameters in response to the variation in at least one positional parameter;
   a detector configured to calculate the variations in at least one positional parameter;
   wherein the controller is configured to controllably adjust in real-time the one or more operational parameters in response to the variation in at least one positional parameter to cause at least one of a new non-zero treatment rate and a new treatment pattern;
   wherein the one or more operational parameters for the light beam include a diameter at the tissue surface in a range less than about 500 micrometers, and a treatment density in a range between about 100 and about 2000 discrete treatment zones per square centimeter per handpiece pass over a given tissue area; and
   further comprising a scanning mechanism, wherein the controller is configured to controllably adjust a scan parameter of the scanning mechanism to compensate for a change in the at least one positional parameter.

2. The apparatus of claim 1, wherein the tissue treatment is pre-selected, and the controller controllably adjusts in real-time the one or more operational parameters in order to continue the pre-selected tissue treatment.

3. The apparatus of claim 1, wherein the one or more operational parameters for the light beam include a separation distance between adjacent discrete treatment zones of greater than about 75 micrometers.

4. The apparatus of claim 1, wherein the detector is at least one of an accelerometer, an optical detector array, a capacitive sensor array, a profilometer and an optical navigation sensor.

5. The apparatus of claim 1, wherein the scanning mechanism includes at least one of a galvanometer, a piezoelectric, a mechanical scanning element, a MEMS element, nanotechnology, a rotating mirror, a rotating optical element, a holographic element, a counter-rotating wheel, a diffractive element, and an acousto-optical element.

6. The apparatus of claim 1, wherein the scanning mechanism and the controller are configured to cause at least one of an angular beam deviation and a translational beam motion.

7. The apparatus of claim 1, wherein the detector is configured to detect a presence of a contrast-enhancing substance applied to a target treatment portion, and wherein the controller and the scanner are configured to cause the light beam to treat only the target treatment portion.

8. The apparatus of claim 1, wherein the light beam has a wavelength in a range between about 700 nm and about 3000 nm, the light beam is pulsed at a frequency in a range less than about 50,000 pulses per second, the light beam has an energy per pulse in a range between about 1 mJ and about 1 J, and the light beam has an optical fluence in a range between about 10 J/cm$^2$ and about 1000 J/cm$^2$.

9. The apparatus of claim 1, wherein the detector is configured to optically measure at least one of speed and velocity when used with a contrast enhancing agent.

10. A method for delivering a pre-selected dermatological tissue treatment comprising the steps of:
    applying a contrast-enhancing substance to an area of tissue to be treated, wherein the tissue comprises human skin;
    emitting at least one light beam from a handpiece towards the area of tissue to be treated, the light beam having at least one operational parameter affecting a dosage of a pre-selected tissue treatment;
    moving the handpiece across the area of tissue, wherein, during the moving, the handpiece receives the at least one light beam and delivers the at least one light beam to the area of tissue to be treated in a pattern of discrete treatment zones; the movement of the handpiece is defined by at least one variable positional parameter; and that variation in at least one positional parameter affects the dosage of the tissue treatment;
    measuring in real-time a variation in at least one positional parameter, wherein the measuring includes detecting the contrast-enhancing substance; and
    controllably adjusting in real-time the at least one operational parameters in response to the variation in at least one positional parameter to adjust a treatment rate in order to continue a pre-selected tissue treatment.

11. The method of claim 10, wherein measuring in real-time variations in at least one positional parameters comprises detecting variation in a parameter selected from the group consisting of a velocity of the handpiece relative to the tissue to be treated, a speed of the handpiece relative to the tissue to be treated, a distance from the handpiece to the tissue to be treated, and a position of the handpiece relative to the tissue to be treated.

12. The method of claim 10, wherein adjusting in real-time at least one operational parameter comprises modifying a light source of the light beam to adjust at least one parameter selected from the group consisting of a power level, a light beam intensity, a pulsation rate, a treatment temperature, and modifying at least one of a position and an angle of a handpiece delivery element.

13. The method of claim 10, wherein controllably adjusting the at least one operational parameters adjusts the treatment rate whereby the pre-selected tissue treatment can continue at a pre-determined dosage.

14. The method of claim 10, wherein controllably adjusting includes scanning the at least one light beam in a manner that limits blurring at least one of the discrete treatment zones.

15. The method of claim 10, wherein the pattern of discrete treatment zones is characterized by a density of treatment zones, and controllably adjusting the at least one operational parameters adjusts the treatment rate whereby the pre-selected tissue treatment can continue at a pre-determined density of treatment zones.

16. The method of claim 10, wherein the step of applying a contrast enhancing agent comprises the step of topically applying the contrast enhancing agent.

17. The method of claim 10, wherein the contrast enhancing agent applied during the applying step makes the measuring step more robust by improving accuracy of the measuring the variation in at least one positional parameter, wherein the at least one positional parameter is selected from the group consisting of a speed, a velocity, or a change in position of the handpiece relative to the treatment area.

18. The method of claim 10, wherein the contrast-enhancing substance includes at least one of a plurality of particles, a suspension, a colloid, an emulsion, a dye and a solution.

19. A method for delivering a pre-selected tissue treatment comprising the steps of:
applying a contrast-enhancing substance to an area of tissue to be treated;
emitting at least one light beam from a handpiece towards the tissue to be treated, the light beam having at least one operational parameter affecting a dosage of a pre-selected tissue treatment;
moving the handpiece across the area of tissue, wherein, during the moving, the handpiece receives the at least one light beam and delivers the at least one light beam to the area of tissue to be treated in a pattern of discrete treatment zones, the movement of the handpiece is defined by at least one variable positional parameter and that variation in at least one positional parameter affects the dosage of the tissue treatment;
measuring in real-time a variation in at least one positional parameter, wherein the measuring includes detecting the contrast-enhancing substance; and
controllably adjusting in real-time the at least one operational parameters in response to the variation in at least one positional parameter to adjust a treatment rate in order to continue a pre-selected tissue treatment,
wherein the contrast-enhancing substance is applied to a target tissue treatment area, and the at least one operational parameters are controllably adjusted to cause the at least one light beam to be directed only to the target tissue treatment area.

20. The method of claim 10, wherein measuring in real-time a variation in at least one positional parameters comprises detecting variation in a parameter selected from the group consisting of a velocity of the handpiece relative to the tissue to be treated, a speed of the handpiece relative to the tissue to be treated, and a position of the handpiece relative to the tissue to be treated.

21. The method of claim 10, wherein controllably adjusting in real-time the at least one operational parameter comprises modifying a light source of the light beam to adjust at least one parameter selected from the group consisting of a power level, a light beam intensity, a pulsation rate, a treatment rate, a treatment temperature, and modifying at least one of a position and an angle of a handpiece delivery element.

22. The method of claim 10, wherein controllably adjusting in real time the at least one operational parameters adjusts the treatment rate whereby the pre-selected tissue treatment can continue at a pre-determined dosage.

23. The method of claim 10, wherein the step of emitting at least one light beam from a handpiece towards the area of tissue to be treated comprises scanning the at least one light beam, and the step of controllably adjusting the at least one operational parameters causes at least one of an angular beam deviation of the at least one light beam and a translational beam motion of the at least one light beam.

24. An apparatus for controlled tissue treatment comprising:
a light emitter that emits at least one light beam;
a moveable handpiece adapted to deliver the at least one light beam to an area of tissue to be treated in a pattern of discrete treatment zones during movement of the handpiece across the area of tissue, wherein a tissue treatment depends upon one or more operational parameters of the at least one light beam, and the movement of the handpiece across the area of tissue is defined by a plurality of variable positional parameters such that variation in at least one positional parameter affects the tissue treatment;
a controller operably coupled to the handpiece for controlling the one or more operational parameters in response to the variation in at least one positional parameter;
a detector configured to calculate the variations in at least one positional parameter;
wherein the controller is configured to controllably adjust in real-time the one or more operational parameters in response to the variation in at least one positional parameter to cause at least one of a new non-zero treatment rate and a new treatment pattern;
wherein the one or more operational parameters for the light beam include a diameter at the tissue surface in a range less than about 500 micrometers, and a treatment density in a range between about 100 and about 2000 discrete treatment zones per square centimeter per handpiece pass over a given tissue area; and
wherein the detector is configured to detect a presence of a contrast-enhancing agent that is applied to the area of tissue to be treated.

25. The apparatus of claim 24, further comprising a scanning mechanism, wherein the controller is configured to controllably adjust a scan parameter of the scanning mechanism to compensate for a change in the at least one positional parameter.

* * * * *